(12) United States Patent
Rosenberg et al.

(10) Patent No.: US 7,655,445 B2
(45) Date of Patent: Feb. 2, 2010

(54) METHODS FOR SYNTHESIS OF SULFATED SACCHARIDES

(75) Inventors: Robert D. Rosenberg, Cambridge, MA (US); Kuberan Balagurunathan, Salt Lake City, UT (US)

(73) Assignee: Massachusetts Institute of Technology, Cambridge, MA (US)

( * ) Notice: Subject to any disclaimer, the term of this patent is extended or adjusted under 35 U.S.C. 154(b) by 406 days.

(21) Appl. No.: 10/986,058

(22) Filed: Nov. 12, 2004

(65) Prior Publication Data

US 2005/0255562 A1 Nov. 17, 2005

Related U.S. Application Data

(60) Provisional application No. 60/518,658, filed on Nov. 12, 2003.

(51) Int. Cl.
| | |
|---|---|
| C12P 19/04 | (2006.01) |
| C12P 19/00 | (2006.01) |
| C12P 1/00 | (2006.01) |
| A01N 41/08 | (2006.01) |
| A61K 31/70 | (2006.01) |
| A61K 31/715 | (2006.01) |
| A61K 31/726 | (2006.01) |
| A61K 31/727 | (2006.01) |

(52) U.S. Cl. ............... 435/101; 435/41; 435/72; 435/849; 514/23; 514/56; 514/62

(58) Field of Classification Search ............... None
See application file for complete search history.

(56) References Cited

U.S. PATENT DOCUMENTS

| | | | |
|---|---|---|---|
| 4,756,884 | A | 7/1988 | Hillman et al. |
| 4,861,712 | A | 8/1989 | Bartl et al. |
| 4,946,775 | A | 8/1990 | Yin |
| 5,059,525 | A | 10/1991 | Bartl et al. |
| 5,110,727 | A | 5/1992 | Oberhardt |
| 5,300,779 | A | 4/1994 | Hillman et al. |
| 6,255,088 | B1 * | 7/2001 | Wong et al. .............. 435/130 |
| 2002/0062019 | A1 * | 5/2002 | Oreste et al. .............. 536/54 |

FOREIGN PATENT DOCUMENTS

| WO | WO 01/02597 | 1/2001 |
|---|---|---|

OTHER PUBLICATIONS

NC-IUBMB, "EC 2.8.2: Sulfotransferases" IUBMB Enzyme Nomenclature, <http://www.chem.qmul.ac.uk/iubmb/enzyme/EC2/8/2/> 2001 (accessed online Apr. 14, 2008), 6 pages.*
Kuberan, B. et al "Rapid Two-Step Synthesis of Mitrin from Heparosan: A Replacement for Heparin" J. Am. Chem. Soc., 2003, 125 (41), pp. 12424-12425 and S1-S10.*
Burkart, M.D. and Wong C.-H. "A Continuous Assay for the Spectrophotometric Analysis of Sulfotransferases Using Aryl Sulfotransferase IV" Analytical Biochemistry, Oct. 1, 1999, 274(1), pp. 131-137.*
M. Manzoni et al. Journal Bioactive Compatible Polymers, 1996, 11, 301-311.
Johansson et al, Biotechnol. Lett., 8 (1986) 421-424.
W. F. Vann, et al "The structure of the capsular polysaccharide (K5 antigen) of urinary-tract-infective *Escherichia coli* 010:K5:H4. A polymer similar to desulfo-heparin." K. Jann, Eur J Biochem 116, 359-64 (1981).
Orellana, C. B., et al "Molecular cloning and expression of a glycosaminoglycan N-acetylglucosaminyl N-deacetylase/N-sulfotransferase from a heparin-producing cell line." J Biol Chem 269, 2270-6 (1994).
J. Li et al., "Biosynthesis of heparin/heparan sulfate. cDNA cloning and expression of D-glucuronyl C5-epimerase from bovine lung." J Biol Chem 272, 28158-63 (1997).
H. Habuchi et al., "The occurrence of three isoforms of heparan sulfate 6-O-sulfotransferase having different specificities for hexuronic acid adjacent to the targeted N-sulfoglucosamine." J Biol Chem 275, 2859-68 (2000).
J. Liu, et al."Purification of heparan sulfate D-glucosaminyl 3-O-sulfotransferase." Journal of Biological Chemistry 271, 27072-27082 (1996).
N. W. Shworak et al., "Multiple isoforms of heparan sulfate D-glucosaminyl 3-O-sulfotransferase. Isolation, characterization, and expression of human cdnas and identification of distinct genomic loci." Journal of Biological Chemistry 274, 5170-5184 (1999).

* cited by examiner

*Primary Examiner*—Christopher R Tate
*Assistant Examiner*—Aaron J Kosar
(74) *Attorney, Agent, or Firm*—Pearl Cohen Zedek Latzer, LLP; Mark S. Cohen

(57) ABSTRACT

The present invention provides methods, processes and reaction mixtures, which produce sulfated heparosan polysaccharides. This invention also provides methods and reaction mixtures for the synthesis of N-deacetylate N-sulfate derivatives of non-sulfated N-acetyl heparosan (HS) polysaccharides.

21 Claims, 7 Drawing Sheets

METHODS FOR SYNTHESIS OF SULFATED SACCHARIDES

CROSS-REFERENCE TO RELATED APPLICATIONS

This Application claims priority from U.S. Provisional Application Ser. No. 60/518,658, filed Nov. 12, 2003, incorporated herein in its entirety.

GOVERNMENT INTEREST STATEMENT

This invention was made in whole or in part with government support under grant number DMI-0303821, awarded by the National Science Foundation. The government may have certain rights in the invention.

FIELD OF THE INVENTION

This invention provides methods for synthesizing sulfated saccharides. Further, this invention provides methods for a rapid synthesis process for sulfated saccharides, with high product yield.

BACKGROUND OF THE INVENTION

Sulfated saccharides play important roles in many biological processes. For example, the sulfated Lea tetra- and pentasaccharides are potent E-selectin inhibitors and sialyl Lewis x with a sulfate group at the 6-position of galactose is a ligand for L-selectin. These sulfated sugars play important roles, among others, in cell adhesion in response to inflammatory reactions. The sulfation of hydroxysteroids provides hydrophilic forms for excretion. Many glycosaminoglycans [GAGs] are sulfated and are involved in numerous cellular functions. GAGs are long linear polysaccharides consisting of disaccharide repeats that contain an amino sugar and are found in most animals. Chondroitin [β(1,4)GlcUA-β(1,3)GalNAc]n and heparin/heparan [α1,4)GlcUA-[β(1,4)GlcNAc]n, (typically with an n=20 to 100) are sulfated at various positions. These GAGs play both structural and recognition roles on the cell surface and in the extracellular matrix.

In the course of oligosaccharide sulfation, 3-Phosphoadenylsulfate, also known as 3'-phosphoadenosine-5'-phosphosulfate (PAPS), is a substrate and cofactor for the enzymatic sulfation of oligosaccharides and steroids via sulfotransferases. Of the twenty-eight sulfotransferase enzymes [EC 2.8.2.1-28] listed in Enzyme Nomenclature 1992, E. C. Webb, ed., Academic Press, San Diego, Calif. 1992, pages 299-303, all but one enzyme utilize PAPS as the sulfate donor. Sulfotransferase activity varies with respect to the donor and/or acceptor compounds with which they work. Known sulfotransferases include those acting on carbohydrate: heparin/heparan sulfate N-sulfotransferase COST); chondroitin 6/keratan 6 sulfate sulfotransferase (C6ST/KSST); galactosylceramide 3'-sulfotransferase; heparan sulfate 2-sulfotransferase (Iduronic acid); HNK-1 sulfotransferase (3-glucuronic acid); heparan sulfate D-glucosamino 3-O-sulfotransferase (3-OST); etc., as well as those acting on phenols, steroids and xenobiotics: aryl sulfotransferase I & II, hydroxy-steroid sulfotransferases I, II & III, dehydroepiandrosterone (DHEA); etc.

The efficiency of oligosaccharide sulfation is limited by PAPS availability as a sulfate donor. PAPS synthesis has been reported, however, the synthesis procedures involve numerous steps with poor yields, which in turn limit the sulfated oligosaccharide product yield.

Despite numerous advances in the chemical synthesis of sulfated oligosaccharides and polysaccharides, to date, existing approaches are cumbersome, time-consuming and inefficient.

SUMMARY OF THE INVENTION

This invention provides, in one embodiment, methods for synthesizing sulfated saccharides.

In one embodiment, there is provided a process for the synthesis of an epimerically enriched form of a sulfated heparosan polysaccharide, comprising reacting the following in a mixture: an acceptor heparosan polysaccharide, a 3'-phosphoadenosine 5'-phosphosulfate (PAPS) sulfate donor, at least one sulfotransferase that catalyzes sulfate transfer from said PAPS sulfate donor to said acceptor heparosan polysaccharide, a p-nitrophenyl sulfate donor, an aryl sulfatase that catalyzes sulfate transfer from said p-nitrophenyl sulfate donor to PAP, thereby regenerating PAPS and an epimerase that catalyzes conversion of said acceptor heparosan polysaccharide to its epimer, thereby synthesizing an epimerically enriched form of a sulfated heparosan polysaccharide.

In one embodiment, the acceptor heparosan polysaccharide is characterized by the structure of the formula I:

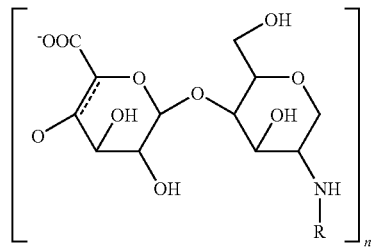

or by the structure of formula II:

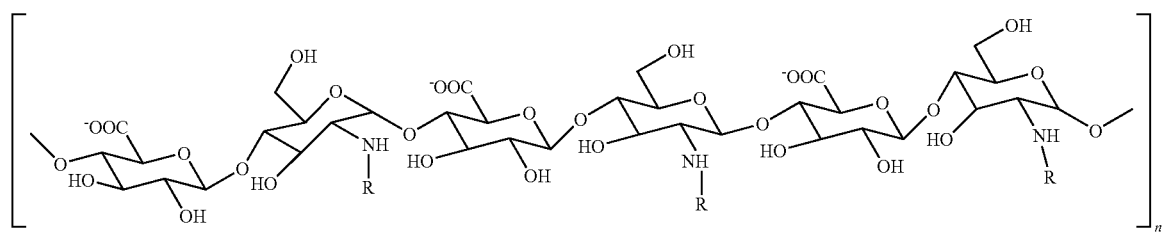

or by the structure of formula III:

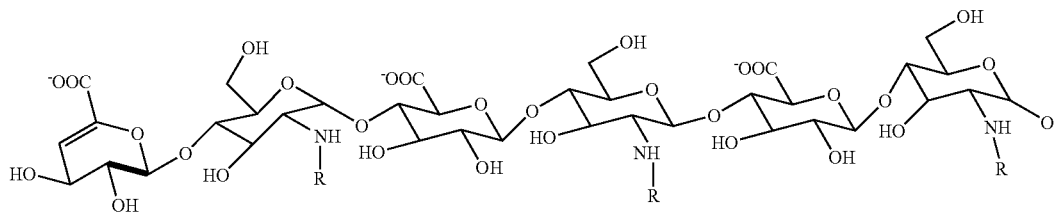

wherein R is a hydrogen, hydroxy, acetyl, alkoxy carbonyl, amido, alkylamido, dialkylamido, nitro, amino, alkylamino, dialkylamino, carboxyl, thio or thioalkyl group, and n is an integer. In another embodiment, the sulfated heparosan polysaccharide product is characterized by the structure of the formula III: $C_n(H_2O)_nR_m$, wherein R is a sulfate group, and n, m are integers.

In another embodiment, the acceptor heparosan polysaccharide is characterized by the structure of the formula IV:

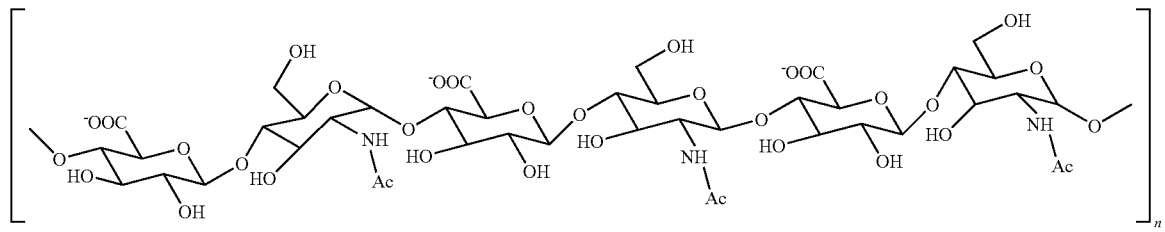

In another embodiment, the invention provides method for producing a sulfated, depolymerized heparosan polysaccharide, comprising reacting the following in a mixture: an acceptor heparosan polysaccharide, a 3'-phosphoadenosine 5'-phosphosulfate (PAPS) sulfate donor, at least one sulfotransferase that catalyzes sulfate transfer from the PAPS donor to the acceptor heparosan polysaccharide, a P-nitrophenyl sulfate donor, an aryl sulfatase that catalyzes sulfate transfer from the P-nitrophenyl sulfate donor to PAPS, thereby regenerating PAPS and an endoglycosidase, which catalyzes cleavage of a glycosidic linkage in said acceptor heparosan polysaccharide, wherein said sulfated heparosan polysaccharide product is diminished in size by at least one monomeric unit of said acceptor heparosan polysaccharide, thereby producing a sulfated depolymerized heparosan polysaccharide.

In another embodiment, this invention provides a reaction mixture for producing a epimerically enriched sulfated heparosan polysaccharide, wherein the reaction mixture comprises: an acceptor heparosan polysaccharide, a 3'-phosphoadenosine 5'-phosphosulfate (PAPS) sulfate donor, at least one sulfotransferase that catalyzes the transfer of a sulfate from the PAPS donor to the acceptor heparosan polysaccharide to produce said sulfated heparosan polysaccharide product, a P-nitrophenyl sulfate donor, an aryl sulfatase that catalyzes the regeneration of PAPS and an epimerase, which catalyzes conversion of said acceptor heparosan polysaccharide to its epimer.

In another embodiment, this invention provides a reaction mixture for producing a sulfated heparosan polysaccharide product, wherein the reaction mixture comprises: an acceptor heparosan polysaccharide, a 3'-phosphoadenosine 5'-phosphosulfate (PAPS) sulfate donor, at least one sulfotransferase that catalyzes the transfer of a sulfate from the PAPS donor to the acceptor heparosan polysaccharide to produce said sulfated heparosan polysaccharide product, a P-nitrophenyl sulfate donor, an aryl sulfatase that catayzes the regeneration of PAPS and at least one endoglycosidase, which catalyzes the cleavage of a glycosidic linkage in a saccharide in said mixture.

In another embodiment, this invention provides a method for synthesizing an N-sulfate derivative of non-sulfated N-acetyl heparosan (HS) polysaccharide represented by the structure of Formula V:

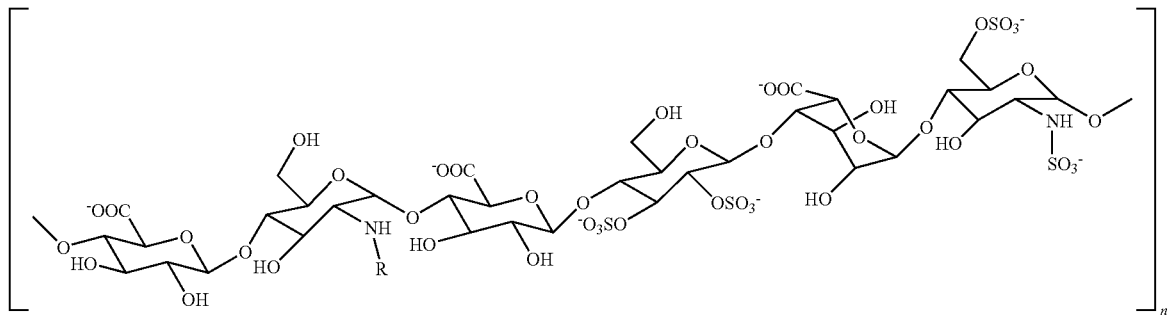

wherein R is an acetyl or sulfate group and n is an integer, comprising reacting in a mixture: an acceptor non-sulfated N-acetyl heparosan (HS) polysaccharide, a 3'-phosphoadenosine 5'-phosphosulfate (PAPS) sulfate donor, an N-deacetylase-N-sulfotransferase that catalyzes sulfate transfer from the PAPS donor to the acceptor polysaccharide, generating an iduronic acid-enriched heparosan polysaccharide, a glucuronosyl C-5 epimerase that catalyzes conversion of the acceptor heparosan polysaccharide to its epimer, following N-sulfation, a P-nitrophenyl sulfate donor, an aryl sulfatase that catalyzes sulfate group cleavage from P-nitrophenyl sulfate, wherein said cleaved sulfate group serves to regenerate PAPS, a 6-O sulfotransferase (6-OST) that catalyzes O-sulfation on carbon 6 of the acceptor polysaccharide and a 3-O sulfotransferase (3-OST), that catalyzes O-sulfation on carbon 3 of the acceptor polysaccharide, thereby synthesizing N-sulfate derivatives of non-sulfated N-acetyl heparosan (HS) polysaccharides represented by the structure of Formula IV.

In another embodiment, this invention provides a reaction mixture for producing an N-sulfate derivative of non-sulfated N-acetyl heparosan (HS) polysaccharide product, wherein the reaction mixture comprises: an acceptor non-sulfated N-acetyl heparosan (HS) polysaccharide; a 3'-phosphoadenosine 5'-phosphosulfate (PAPS) sulfate donor; an N-deacetylase-N-sulfotransferase that catalyzes sulfate transfer from the PAPS donor to the acceptor polysaccharide, generating an iduronic acid-enriched heparosan polysaccharide; a glucuronosyl C-5 epimerase that catalyzes conversion of the acceptor heparosan polysaccharide to its epimer, following N-sulfation; a P-nitrophenyl sulfate donor; an aryl sulfatase that catalyzes sulfate group cleavage from P-nitrophenyl sulfate, wherein said cleaved sulfate group serves to regenerate PAPS; a 6-O sulfotransferase (6-OST) that catalyzes O-sulfation on carbon 6 of the acceptor polysaccharide; and (h) 3-O sulfotransferase (3-OST), that catalyzes O-sulfation on carbon 3 of the acceptor polysaccharide.

DETAILED DESCRIPTION OF THE INVENTION

Figure 1:
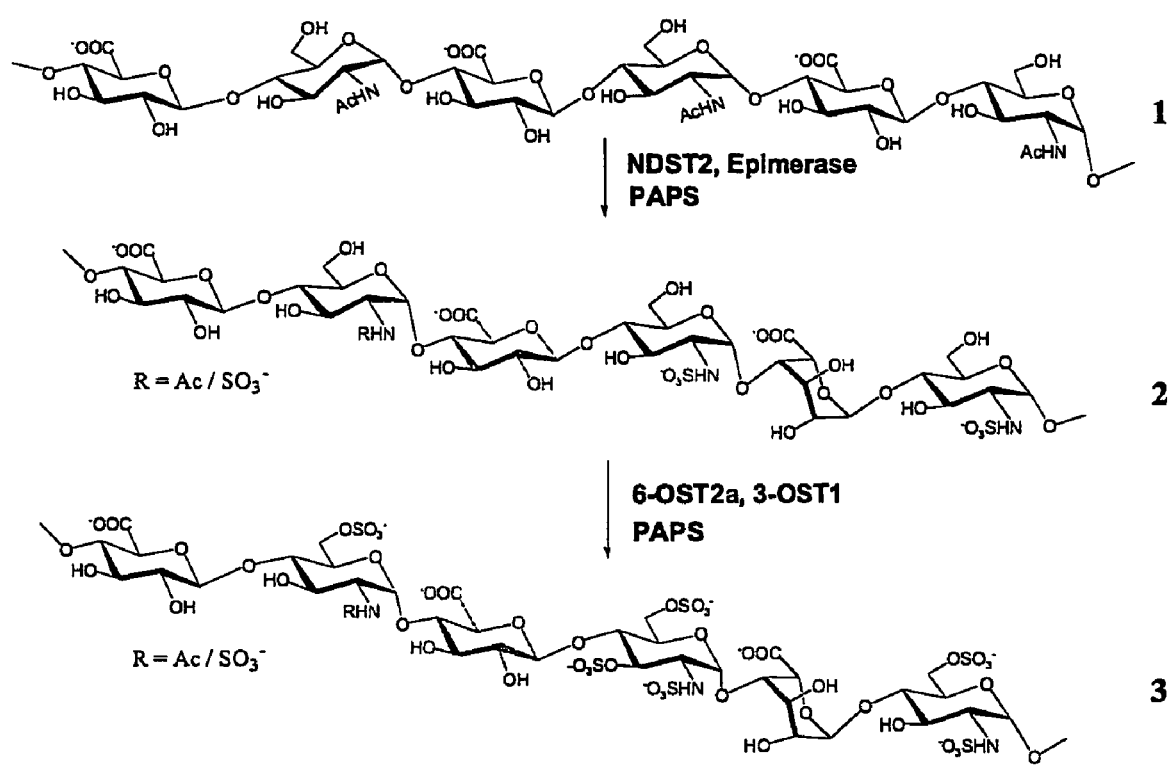
FIG. 1 schematically depicts the enzymatic synthesis of N-deacetylate N-sulfate derivatives of non-sulfated N-acetyl heparosan (HS) polysaccharides.

This invention provides, in one embodiment, a rapid, high-yield process for synthesis of sulfated heparosan polysaccharides.

In one embodiment, there is provided a process for the synthesis of an epimerically enriched form of a sulfated heparosan polysaccharide, comprising reacting the following in a mixture: an acceptor heparosan polysaccharide with a 3'-phosphoadenosine 5'-phosphosulfate (PAPS) donor, at least one sulfotransferase that catalyzes sulfate transfer from the PAPS donor to the acceptor heparosan polysaccharide, a p-nitrophenyl sulfate donor and an aryl sulfatase that catalyzes sulfate transfer from the p-nitrophenyl sulfate donor to PAPS, regenerating PAPS, and an epimerase that catalyzes conversion of said acceptor heparosan polysaccharide to its epimer thereby synthesizing an iduronic acid enriched form of a sulfated heparosan polysaccharide.

In another embodiment, this invention provides a reaction mixture for producing an epimerically enriched form of a sulfated heparosan polysaccharide, wherein the reaction mixture comprises: an acceptor heparosan polysaccharide, a 3'-phosphoadenosine 5'-phosphosulfate (PAPS) sulfate donor, at least one sulfotransferase that catalyzes the transfer of a sulfate from the PAPS donor to the acceptor heparosan polysaccharide to produce the sulfated heparosan polysaccharide product, a p-nitrophenyl sulfate donor, an aryl sulfatase that catayzes the regeneration of PAPS and an epimerase, which catalyzes conversion of the acceptor heparosan polysaccharide to its epimer.

The term "saccharide", in one embodiment, refers to a carbohydrate, also known as a sugar, which is a broad term for a chemical compound comprised of carbon hydrogen and oxygen, wherein the number of hydrogen atoms is essentially twice that of the number of oxygen atoms. In another embodiment, the number of repeating units may vary in a saccharide. Thus disaccharides, oligosaccharides and polysaccharides are all examples of chains composed of saccharide units, which vary in length, and represent separate embodiments of this invention. The assembly into chains may be in any order, in another embodiment, and the linkage between two saccharide units may occur in any of at least ten different ways, each of which represents a separate embodiment of this invention. It is to be understood that the synthesis of any such compound via the methods/processes described herein is to be considered an embodiment of this invention.

The acceptor heparosan polysaccharide may be any heparosan polysaccharide wherein its sulfation is desired, which comprises at least two different monomers. The saccharide may be a di, penta-, oligo- or polysaccharide. The acceptor heparosan polysacchalide may comprise, for example, a heparin, or any sulfated version of the same.

The acceptor heparosan polysaccharide may be represented, in one embodiment, by the structure of the formula I, which is as follows:

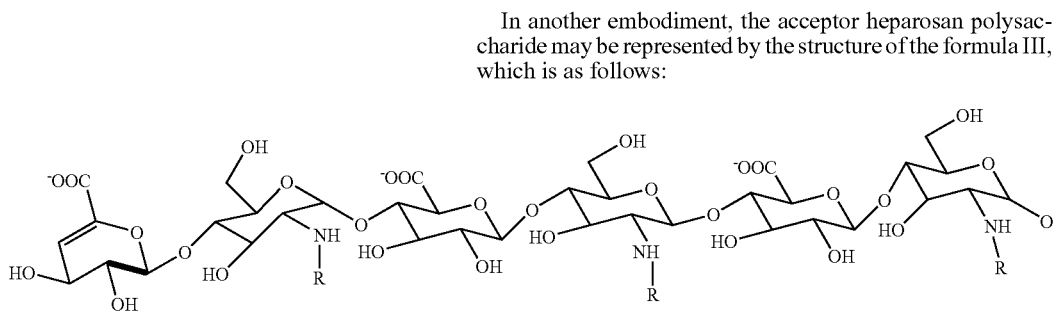

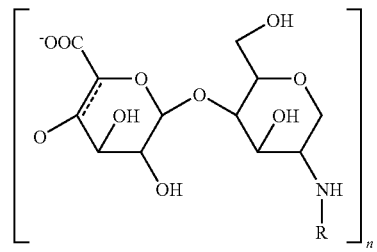

In another embodiment, the acceptor heparosan polysaccharide may be represented by the structure of the formula II, which is as follows:

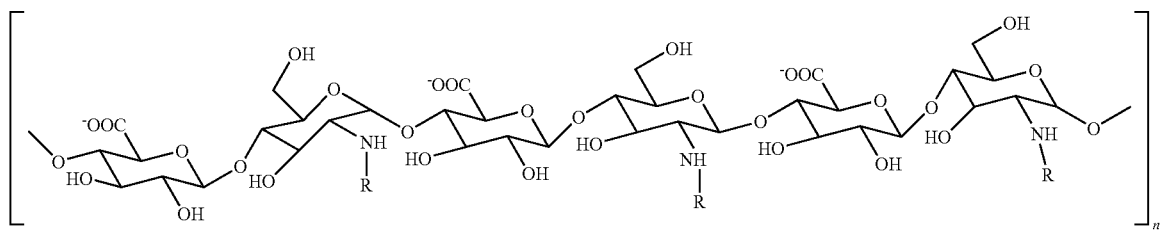

In another embodiment, the acceptor heparosan polysaccharide may be represented by the structure of the formula III, which is as follows:

According to this aspect of the invention, in one embodiment, R is a hydrogen, or in another embodiment, R is a hydroxy, or in another embodiment, R is an acetyl, or in another embodiment, R is an alkoxy carbonyl, or in another embodiment, R is an amido, or in another embodiment, R is an alkylamido, or in another embodiment, R is a dialkylamido, or in another embodiment, R is a nitro, or in another embodiment, R is a amino, or in another embodiment, R is an alkylamino, or in another embodiment, R is a dialkylamino, or in another embodiment, R is a carboxyl, or in another embodiment, R is a thio, or in another embodiment, R is a thioalkyl group. In another embodiment, the acceptor heparosan polysaccharide may be unsubstituted or substituted by one or more groups, as described. In another embodiment, the acceptor heparosan polysaccharide may comprise mixed substitutions of any of the groups herein.

In another embodiment, the acceptor heparosan polysaccharide is an N-acetyl heparosan (HS). In one embodiment, the N-acetyl heparosan acceptor heparosan polysaccharide is represented by the structure of Formula IV.

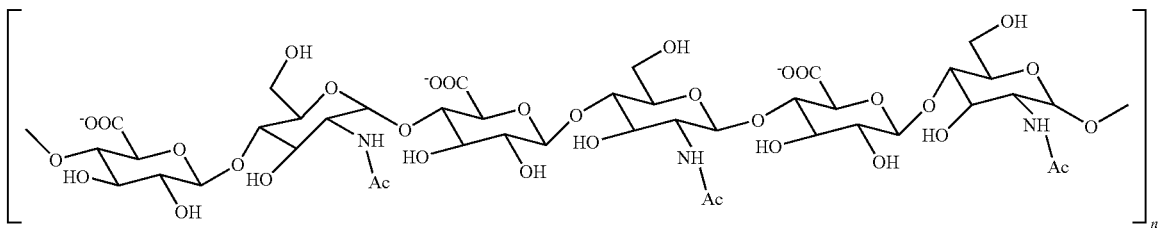

According to this aspect of the invention, n is an integer. In one embodiment n comprises a value of between 50-250. In another embodiment, n comprises a value of between 1-1,000, or, in another embodiment, 1-100, or in another embodiment, 1-50, or in another embodiment, 1-25, or in another embodiment, 1-15. In another embodiment, n comprises a value of between 100-1,000,000. In another embodiment, n comprises a value of between 100-100,000. In another embodiment, n comprises a value of between 100-1,000. In another embodiment, n comprises a value of between 1,000-1,000,000, or in another embodiment, 1,000-100,000 or in another embodiment, 1,000-50,000, or in another embodiment, 1,000-25,000, or in another embodiment, 1,000-10,000.

In another embodiment, the Heparosan polysaccharide is a K5 polysaccharide, which may be obtained by fermentation of wild or cloned K5 producing *Escherichia coli* strains (See, for example, M. Manzoni et al. Journal Bioactive Compatible Polymers, 1996, 11, 301-311 or in WO 01/02597) Heparosan like polysaccharides may also be obtained from *Pasturella multocida*, as described (DeAngelis PL, et al., Carbohydrate Research, (2002) 337(17): 1547-52). In another embodiment, the starting material may comprise Acharan Sulfate, and may be isolated from an African giant snail and utilized accordingly.

In another embodiment, the acceptor heparosan polysaccharides may have a low molecular weight, with a distribution of from about 1,500 to about 15,000 Daltons (Da), or, in another embodiment, from about 2000 to about 9,000 Da with a mean molecular weight of about 5,000 Da, or, in another embodiment, a higher molecular weight, particularly with a distribution from about 10,000 to about 50,000 Da, or, in another embodiment, from about 20,000 to about 40,000 Da with a mean molecular weight of about 30,000 Da. In another embodiment, the acceptor heparosan polysaccharides may have a molecular weight distribution from about 1,500 to about 50,000 Da, with a mean molecular weight of 20,000-25,000 Da.

In another embodiment, the acceptor heparosan polysaccharide may comprise an iduronic acid-enriched polysacchalide. In another embodiment, the acceptor heparosan polysaccharide may comprise a glucuronic acid-enriched polysaccharide.

In one embodiment, the acceptor heparosan polysaccharide is at a final concentration of 0.1-1 mM, or in another embodiment, the acceptor heparosan polysaccharide is at a final concentration of 1-2.5 mM, or in another embodiment, the acceptor heparosan polysaccharide is at a final concentration of 2.5-10 mM, or in another embodiment, the acceptor heparosan polysaccharide is at a final concentration of 10-25 mM, or in another embodiment, the acceptor heparosan polysaccharide is at a final concentration of 10-50 mM, or in another embodiment, the acceptor heparosan polysaccharide is at a final concentration of 25-50 mM, or in another embodiment, the acceptor heparosan polysaccharide is at a final concentration of 50-75 mM, or in another embodiment, the acceptor heparosan polysaccharide is at a final concentration of 25-75 mM, or in another embodiment, the acceptor heparosan polysaccharide is at a final concentration of 50-100 mM, or in another embodiment, the acceptor heparosan polysaccharide is at a final concentration of 75-100 mM in the reaction mixture. In another embodiment, the acceptor heparosan polysaccharide is at a final concentration of 0.1-100 mM in the reaction mixture.

Sulfated heparosan polysaccharides are produced via the methods of this invention, as a result of sulfotransferase activity, which catalyzes sulfate transfer from the PAPS donor to the acceptor heparosan polysacchalide. In one embodiment, the sulfotransferase is an N-deacetylase-N-sulfotransferase, or in another embodiment, the sulfotransferase is a heparin/heparin sulfate N-sulfotransferase, or in another embodiment, the sulfotransferase is a heparin sulfate 2-sulfotransferase, or in another embodiment, the sulfotransferase is a 6-O sulfotransferase, or in another embodiment, the sulfotransferase is a 3-O sulfotransferase, or in another embodiment, the sulfotransferase is a 2-O sulfotransferase, or in another embodiment, a combination of sulfotransferases may be utilized in the reaction mixture in the synthesis of the sulfated heparosan polysaccharide product. In another embodiment, the 3-O sulfotransferase may be 3-OST1. In another embodiment, the 6-O sulfotransferase may be 6-OST1,6-OST2 or 6-OST3. In another embodiment, the 6-OST2 may be 6-OST2a or 6-OST2b. It is to be understood that a given sulfotransferase may require a particular acceptor heparosan polysaccharide in order to catalyze transfer of the sulfate group, whose application is well known to one skilled in the art.

In one embodiment, this invention provides a process for synthesizing epimerically enriched forms of sulfated heparosan polysaccharides. According to this aspect of the invention, in one embodiment, the process yields a sulfated heparosan polysaccharide that is enriched for an epimer of its acceptor heparosan polysaccharide, via the inclusion of an epimerase, which catalyzes the conversion. Epimerization occurs, in one embodiment, when uronic acid residues are located at the reducing side of N-sulfated glucosamine residues, of acceptor heparosan polysaccharides. In another embodiment, epimerization and N-sulfation may be coupled, followed by O-sulfation. According to this aspect, the coupling of the two imposes a stereochemical constraint that limits O-sulfation on particular positions in the acceptor heparosan polysaccharide.

In one embodiment, the epimerically enriched form of a sulfated heparosan polysaccharide may comprise at least 60% of heparosan polysaccharides produced via the methods/processes and in the reactions mixtures of this invention. In another embodiment, the epimerically enriched form of a sulfated heparosan polysaccharide may comprise at least 65% of heparosan polysaccharides, or in another embodiment, at least 70% of heparosan polysaccharides, or in another embodiment, at least 75% of heparosan polysaccharides, or in another embodiment, at least 80% of heparosan polysaccharides, or in another embodiment, at least 85% of heparosan polysaccharides, or in another embodiment, at least 90% of heparosan polysaccharides, or in another embodiment, between 90 and 95%, or in another embodiment at least 95%, or in another embodiment, between 95 and 100% of heparosan polysaccharides produced via the methods/processes and in the reactions mixtures of this invention. In another embodiment, the epimerically enriched form of a sulfated heparosan polysaccharide may comprise 100% of heparosan polysaccharides produced via the methods/processes and in the reactions mixtures of this invention.

In another embodiment of this invention, an epimer of the acceptor heparosan polysaccharide produced via the methods/processes and in the reaction mixtures of this invention is further sulfated.

In one embodiment, the epimerase is a glucuronosyl C-5 epimerase. In another embodiment, the glucuronosyl C-5 epimerase utilized for the methods and reaction mixtures of this invention may be a recombinant glucuronosyl C5 epimerase, a glucuronosyl C5 epimerase isolated from murine mastocytomas or a glucuronosyl C5 epimerase extracted from bovine liver.

Sulfonation of the acceptor polysaccharide of this invention is accomplished via the inclusion of sulfotransferases in the reaction mixtures, and according to the methods/processes of this invention. In one embodiment, the sulfotransferase is an N-deacetylase-N-sulfotransferase, heparin/heparin sulfate N-sulfotransferase; heparin sulfate 2-sulfotransferase; 6-O sulfotransferase; 3-O sulfotransferase; 2-O sulfotransferase, any of the enzyme isoforms, or a combination thereof.

In one embodiment, the N-deacetylase-N-sulfotransferase is NDST1, NDST2 or NDST3. In another embodiment, the N-deacetylase-N-sulfotransferase utilized for the synthesis may be a recombinant N-deacetylase-N-sulfotransferase. The recombinant enzymes may be produced in insect cells, in yeast or in bacterial cells, via methods well known to one skilled in the art. In another embodiment, the enzymes may be isolated from any animal cell wherein the enzyme is naturally expressed, or from human cells.

In another embodiment, the 6-O sulfotransferase utilized for the synthesis may be a recombinant enzyme. The recombinant enzymes may be produced in insect cells, in yeast or in bacterial cells, via methods well known to one skilled in the art. In another embodiment, the enzymes may be isolated from any animal cell wherein the enzyme is naturally expressed, or from human cells. In one embodiment, the 6-O sulfotransferase utilized may be the 6-OST1, 6-OST2 or 6-OST3 isoform. In another embodiment, 6-OST2 may be 6-OST2a or 6-OST2b.

In another embodiment, the 3-O sulfotransferase utilized for the synthesis may be a recombinant enzyme. The recombinant enzymes may be produced in insect cells, in yeast or in bacterial cells, via methods well known to one skilled in the art. In another embodiment, the enzymes may be isolated from any animal cell wherein the enzyme is naturally expressed, or from human cells. In one embodiment, the 3-O sulfotransferase utilized may be the 3-OST1 isoform, or in another embodiment, the 3-OST5 isoform, with resulting structures/tetrasaccharides considered as part of the present invention.

It is to be understood that more than one sulfotransferase may comprise the reaction mixture, which may, in one embodiment, result in sulfation at varied sites in the acceptor heparosan polysaccharide. In another embodiment, the sulfotransferase may provide for multiple rounds of sulfation of the acceptor heparosan polysaccharide.

A sulfotransferase catalyzes sulfate transfer from 3'-phosphoadenosine 5'-phosphosulfate (PAPS) to an acceptor heparosan polysaccharide. According to this aspect of the invention, an aryl sulfatase catalyzes sulfate transfer from p-nitrophenyl sulfate to regenerate PAPS.

LC/MS analysis of products following a synthesis method facilitating PAPS regeneration resulted in N-sulfated disaccharide production which accounts for at least roughly 90% modification catalyzed by NDST2, whereas the absence of PAPS regeneration provided only roughly 75% conversion (Example 3). Thus, the regeneration of PAPS resulted in greater NDST efficiency. Greater NDST efficiency may be, in one embodiment, as a result of diminished free sulfate availability in the reaction mixture, since it has been shown that free sulfate availability inhibits sulfotransferase activity.

PAPS regeneration may, in one embodiment, diminish free sulfate availability. In another embodiment, the reaction mixture comprises an excess of sulfate donor, as compared to PAPS. In another embodiment, the p-nitrophenyl sulfate donor is at a concentration that is at least one hundred fold in excess of the concentration of PAPS in said mixture. In another embodiment, the p-nitrophenyl sulfate donor is at a concentration that is at least two hundred fold in excess, or in another embodiment, at least two hundred and fifty fold in excess, or in another embodiment, at least five hundred fold in excess, or in another embodiment, at least seven hundred and fifty fold in excess, or in another embodiment, at least one thousand fold in excess, or in another embodiment, at least five thousand fold in excess, or in another embodiment, at least ten thousand fold in excess, or in another embodiment, at least fifty thousand fold in excess, or in another embodiment, at least seventy five thousand fold in excess, or in another embodiment, at least one hundred thousand fold in excess of the concentration of PAPS in said mixture.

In another embodiment, the aryl sulfatase utilized for the synthesis may be a recombinant enzyme. The recombinant enzymes may be produced in insect cells, in yeast or in bacterial cells, via methods well known to one skilled in the art. In another embodiment, the enzymes may be isolated from any animal cell wherein the enzyme is naturally expressed, or from human cells.

In another embodiment, this invention provides a method for producing a sulfated, depolymerized heparosan polysaccharide, comprising reacting the following in a mixture: an acceptor heparosan polysaccharide, a 3'-phosphoadenosine 5'-phosphosulfate (PAPS) sulfate donor, at least one sulfotransferase that catalyzes sulfate transfer from the PAPS donor to the acceptor heparosan polysaccharide, a p-nitrophenyl sulfate donor, an aryl sulfatase that catalyzes sulfate transfer from the p-nitrophenyl sulfate donor to PAPS, thereby regenerating PAPS and an endoglycosidase, which catalyzes cleavage of a glycosidic linkage in the acceptor heparosan polysaccharide, wherein the sulfated heparosan polysaccharide product is diminished in size by at least one monomeric unit of the acceptor heparosan polysaccharide, thereby producing a sulfated depolymerized heparosan polysaccharide.

In another embodiment, this invention provides a reaction mixture for producing a sulfated heparosan polysacchalide product, wherein the reaction mixture comprises: an acceptor heparosan polysaccharide, a 3'-phosphoadenosine 5'-phosphosulfate (PAPS) sulfate donor, at least one sulfotransferase that catalyzes the transfer of a sulfate from the PAPS donor to the acceptor heparosan polysaccharide to produce the sulfated heparosan polysaccharide product, a P-nitrophenyl sulfate donor, an aryl sulfatase that catayzes the regeneration of PAPS and at least one endoglycosidase, which catalyzes the cleavage of a glycosidic linkage in a saccharide in the reaction mixture.

According to this aspect of the invention, in one embodiment, the endoglycosidase catalyzes cleavage of at least one glycosidic linkage in the acceptor heparosan polysaccharide, prior to its sulfation. In another embodiment, the endoglycosidase catalyzes cleavage of at least one glycosidic linkage in the acceptor heparosan polysaccharide, following its sulfation. In another embodiment, the endoglycosidase catalyzes cleavage of glycosidic linkages both prior to and following sulfation. In another embodiment, the endoglycosidase catalyzes cleavage of multiple glycosidic linkages.

In another embodiment, the endoglycosidase is a Heparitinase. In another embodiment, the Heparatinase is Heparitinase I, II or III. In another embodiment, the endoglycosidase is a Glycuronidase. In another embodiment, the Glycuronidase is $\Delta^{4,5}$-Glycuronidase.

In another embodiment, the method of producing a sulfated, depolymerized heparosan polysaccharide, comprises reacting an epimerase with the acceptor heparosan polysaccharide, as well. It is to be understood that any embodiment described, regarding sulfating heparosan polysaccharides of this invention, is to be considered as applicable throughout, and is part of this invention.

In another embodiment the degree of purity of the enzymes employed in the methods and reaction mixtures of the present invention are not critical. The enzymes may, in one embodiment, be present in crystalline form.

The purification and isolation of sulfotransferases, aryl sulfatases, endoglycosidases and epimerases are well described in the literature, and methods thereof are well known to one skilled in the art. The enzymes may be produced via recombinant techniques, in another embodiment. In another embodiment, recombinant enzymes may be engineered such that one or more of the amino acid residues in the amino acid sequence of the enzyme are changed in order to optimize the properties of the enzyme, such as, for example, enzyme thermostability, catalytic efficiency or regioselectivity, each of which represents an additional embodiment of this invention.

The enzymes may be used in one embodiment, in soluble form or, in another embodiment, they may be immobilized by adsorption, encapsulation, chelation, precipitation or covalent binding to a solid support, such as a polymeric substance, or a derivative thereof which is insoluble in protic or aprotic solvents (Methods in Enzymology, vol. 44, Academic Press, 1976), each of which represents an additional embodiment of this invention. If the enzymes are used in soluble form, they may, in another embodiment, first be chemically modified in a suitable manner in order to, in one embodiment, increase their thermostability, or, in another embodiment, increase their stability. In another embodiment, enzymes may be immobilized to an insoluble polymer, which may be readily separated from the product mixture, enabling reuse of the enzymes. In one embodiment, the polymer comprises agarose, or in another embodiment, the polymer comprises cellulose, or in another embodiment, the polymer comprises hydroxyethyl acrylate, or in another embodiment, the polymer comprises glass, or in another embodiment, the polymer comprises silica, or in another embodiment, the polymer comprises polyacrylic amide, or in another embodiment, the polymer comprises polyacrylate-based plastics. In another embodiment, immobilization on an insoluble polymer provides for protection/stabilization from elevated temperatures and organic cosolvents used in the methods of this invention.

In one embodiment, the reaction conditions may be carried out under buffer conditions ranging in pH value from 4.5-9.

In another embodiment, the reaction is carried out in a buffered solution comprising 4-morpholine propane sulfonic acid (MES). MES concentration may range from 10 mM-100 mM. In one embodiment, a 25 mM final concentration of MES is utilized in the reaction mixture.

The reaction mixture may further comprise small amounts of Triton X-100. In one embodiment, a final concentration of 0.05% of Triton X-100 is used in the reaction mixture. In another embodiment, the concentration of Triton X-100 utilized ranges from 0.0001%-1%.

The reaction mixture will further comprise divalent cations. In one embodiment, the reaction mixture comprises $MgCl_2$. In one embodiment, $MgCl_2$ is at a final concentration of 2.5 μM, in the reaction mixture. In another embodiment, the reaction mixture comprises $CaCl_2$. In another embodiment, $CaCl_2$ is at a final concentration of 1.2 μM in the reaction mixture. In another embodiment, alternative divalent cations are utilized, as is well known in the art. In another embodiment, the reaction mixture comprises bovine sera albumin (BSA). In one embodiment, BSA is at a final concentration of 0.025 mg/ml in the reaction mixture.

In one embodiment, reaction conditions may be changed, to optimize conditions for the synthesis of a sulfated saccharide. In one embodiment, the temperature at which the reaction is carried out may be varied, as may be the pH, the buffer utilized, and/or the concentration of the reactants. Such conditions may be varied in order for a variety of purposes, such as ease of use, optimization of yield, enzyme performance, as will be appreciated by one skilled in the art.

For example, the reaction temperature may be varied, in one embodiment, in order to influence product yield and/or enzyme stability. The temperature of the reaction mixture may be, in one embodiment, at 37° C., during the reaction. In another embodiment, the temperature of the reaction mixture may be between 30 and 40° C. Higher temperatures may be used, in another embodiment. In another embodiment, thermostable enzymes and substrates, and/or enzymes stabilized against thermal denaturation by employing, for example, high substrate concentrations (Johansson et al, Biotechnol. Lett., 8 (1986) 421-424) are employed. According to this aspect of the invention, a high temperature may provide for the use of high substrate concentration, which may increase product yield. In another embodiment, high temperature results in an increase in enzyme activity, which in turn results in shorter reaction times for product synthesis. It is to be understood that the upper temperature limit of the reaction conditions will be determined by the thermostability of the enzyme in the reaction medium.

In another embodiment, the reaction may be carried out for a time comprised of between 1 and 24 hours. In one embodiment, the reaction mixture is incubated for 12 hours.

The reaction may be stopped by dilution with DEAE wash buffer and subsequent product purification on a DEAE column. In another embodiment, the reaction is stopped by heating the reaction mixture at 70° C. followed by centrifugation at 10,000 g for 3 minutes.

The method/process for synthesis of sulfated heparosan polysaccharides, as described herein, in one embodiment, is simple in its requirement of a single reaction mixture to achieve sulfation. According to this aspect of the invention, use of a single reaction mixture may provide greater efficiency in sulfated saccharide synthesis. Further, the method may provide for greater yields, in comparison to chemical synthetic methods.

Synthesis of a given sulfated heparosan polysaccharide by the methods described herein may be determined by methods well described in the art, including immunoblot analysis, HPLC, Mass Spectroscopy, functional assays to detect the sulfated heparosan polysaccharide product, such as, for example, in the case of heparin synthesis, demonstrating anticoagulant activity. Other assays for detection of the synthesis of sulfated heparosan polysaccharide, such as HPLC, Mass Spectroscopy, chromatography, and others are well known to those skilled in the art, and represent additional embodiments of this invention.

In one embodiment, the sulfated heparosan polysaccharide is represented by the structure of formula V:

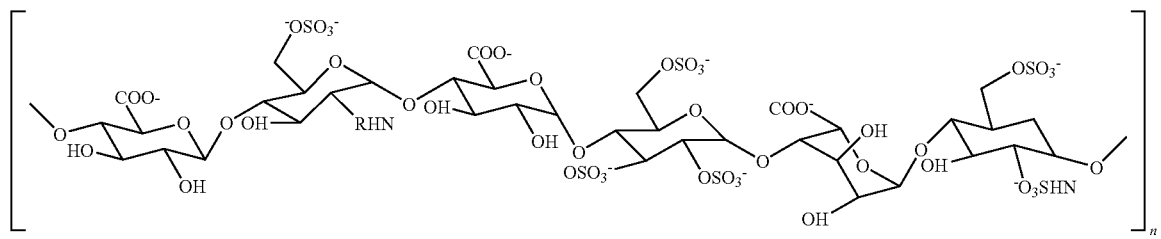

wherein R is an acetyl or sulfonate group, and n is an integer.

In another embodiment, the sulfated heparosan polysaccharide is represented by the structure of the formula VI:

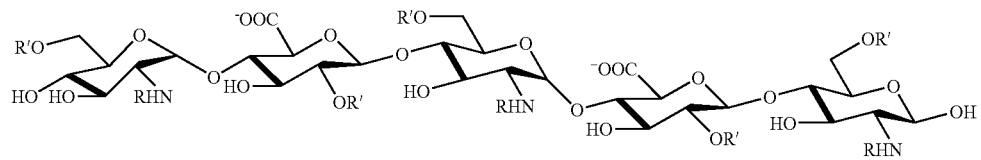

wherein R is an acetyl or sulfate group, and R' or R" is a hydrogen or an sulfate group.

In another embodiment, the sulfated heparosan polysaccharide is represented by the structure of the formula VII:

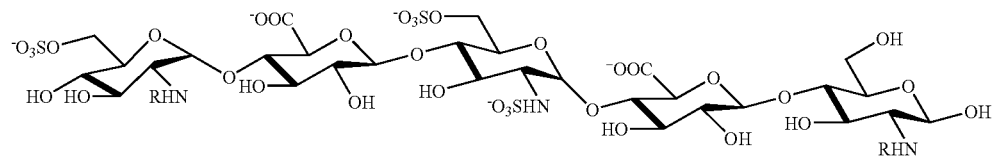

wherein R is a hydrogen, or an a acetyl or sulfate group.

In another embodiment, the sulfated heparosan polysaccharide is represented by the structure of the formula VIII:

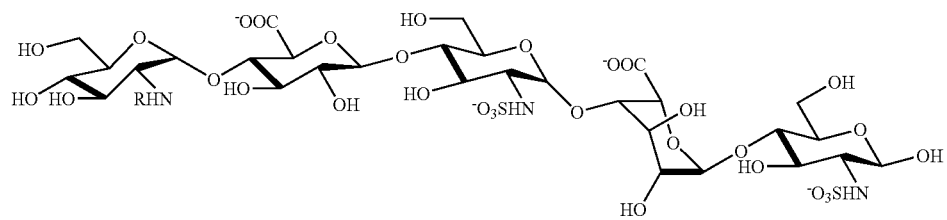

In another embodiment, the sulfated heparosan polysaccharide is represented by the structure of the formula IX:

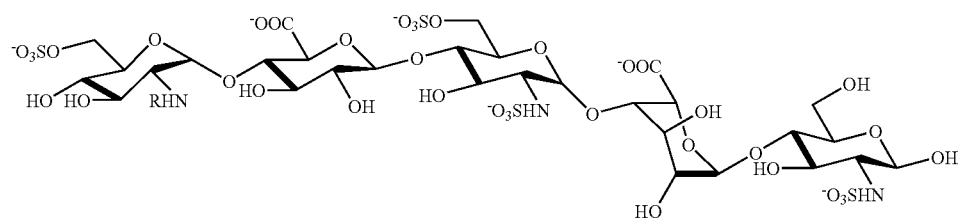

In another embodiment, the sulfated heparosan polysaccharide is represented by the structure of the formula X:

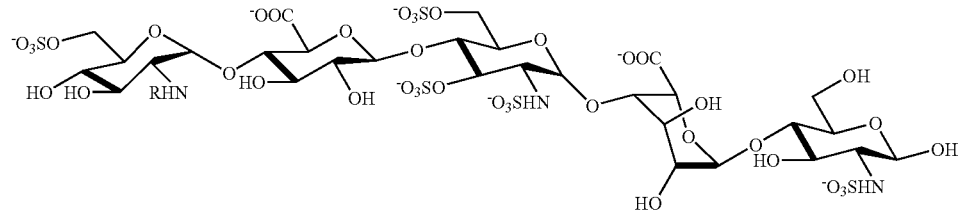

In another embodiment, this invention provides a method for synthesizing an epimerically enriched N-sulfate derivative of non-sulfated N-acetyl heparosan (HS) polysaccharide represented by the structure of Formula V:

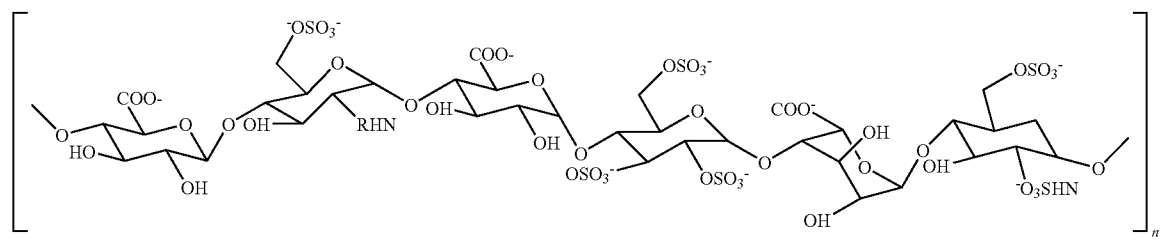

wherein R is an acetyl or sulfate group and n is an integer, comprising reacting the following in a mixture: an acceptor non-sulfated N-acetyl heparosan (HS) polysaccharide, a 3'-phosphoadenosine 5'-phosphosulfate (PAPS) sulfate donor, an N-deacetylase-N-sulfotransferase that catalyzes sulfate transfer from said PAPS donor to said acceptor polysaccharide, generating an iduronic acid-enriched heparosan polysaccharide, a glucuronosyl C-5 epimerase that catalyzes conversion of said acceptor heparosan polysaccha-lide to its epimer, following N-sulfation, a p-nitrophenyl sulfate donor, an aryl sulfatase that catalyzes sulfate group cleavage from p-nitrophenyl sulfate, wherein said cleaved sulfate group serves to regenerate PAPS, a 6-O sulfotransferase (6-OST) that catalyzes O-sulfation on carbon 6 of the acceptor polysaccalide and a 3-O sulfotransferase (3-OST), that catalyzes O-sulfation on carbon 3 of the acceptor polysaccharide, thereby synthesizing epimerically enriched N-sulfate derivatives of non-sulfated N-acetyl heparosan (HS) polysaccharides represented by the structure of Formula IV.

In one embodiment, epimerically enriched N-sulfate derivatives of non-sulfated N-acetyl heparosan (HS) polysaccharides represented by the structure of Formula V, refers to a molecule that corresponds to the following formula:

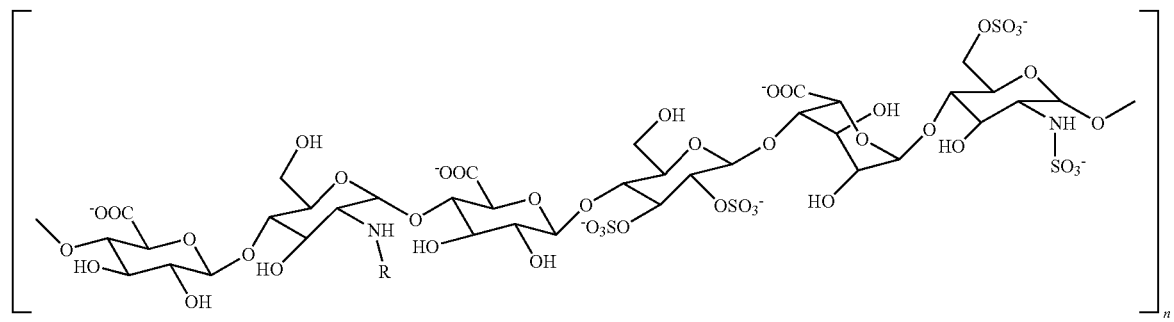

wherein R is an acetyl or sulfonate group, and n is an integer.

In one embodiment, the compound of Formula V has an acetyl group (Ac) at each position indicated by an R in the formula hereinabove. In another embodiment, the compound has a sulfonate group ($SO_3^-$) at each position indicated by an R in the formula hereinabove. In another embodiment, the compound has a Hydrogen (H) at each position indicated by an R in the formula hereinabove. In another embodiment, the compound has mixed substitutions of Ac $SO_3^-$ or H groups at positions indicated by an R in the formula hereinabove. It is to be understood that any substitutions of formula IV achieved via the methods described herein, with anti-coagulant activity are to be considered as part of this invention. Such compounds may have additional therapeutic activity, as well, including antiviral activity.

In another embodiment, n is an integer with a value of 50-250. In one embodiment, n is an integer with a value of 1-1,000, or, in another embodiment, 1-100, or in another embodiment, 1-50, or in another embodiment, 1-25, or in another embodiment, 1-15. In another embodiment, n is an integer with a value of 100-1,000,000. In another embodiment, n is an integer with a value of 100-100,000. In another embodiment, n is an integer with a value of 100-1,000. In another embodiment, n is an integer with a value of 1,000-1,000,000, or in another embodiment, 1,000-100,000 or in another embodiment, 1,000-50,000, or in another embodiment, 1,000-25,000, or in another embodiment, 1,000-10,000.

As described hereinabove, ascertaining procurement of the product by the synthesis method described herein may be via methods well described in the art, some examples of which are described herein.

In one embodiment, the term derivative is meant to encompass any molecule that is a product of the manipulation of an index compound, via any of the steps comprising the synthesis method disclosed herein. A derivative of non-sulfated N-acetyl heparosan (HS) polysaccharide, therefore, indicates that the index compound, in this case the N-acetyl heparosan (HS) polysaccharide, is a starting material, and following the synthesis method outlined herein, the product is referred to as a derivative of non-sulfated N-acetyl heparosan (HS) polysaccharide.

In one embodiment, the derivative will, following the synthesis outlined herein, be characterized by the structure of formula V.

In another embodiment, the products obtained via the methods/processes of this invention result in a greater than 80% product yield. In another embodiment, the product yield is greater than 83%, or in another embodiment, the product yield is greater than 85%, or in another embodiment, the product yield is greater than 87%, or in another embodiment, the product yield is greater than 90%, or in another embodiment, the product yield is greater than 93%, or in another embodiment, the product yield is greater than 95%.

The products synthesized by the methods provided herein, may have any number of biologic functions. In one embodiment, the compounds produced may exhibit anticoagulant activity.

As described hereinabove, functional assays may be utilized to determine product synthesis, thus methods for measuring anticoagulant activity, may be used for some products synthesized by the methods described herein. Some methods for measuring anticoagulant activity include, in one embodiment, measuring the effect on coagulation and/or the concentration in blood or plasma of direct or, in another embodiment, of indirect inhibitors of activated coagulation factors, including the assessment of inhibition of coagulation factors (e.g. FIIa and FXa). Non-limiting examples of such methods include the use of chromogenic substrate analysis and so-called "clotting methods", e.g. the aPTT assay (activated partial thromboplastin time), the ACT assay (activated clotting time), the TT assay (thrombin time), the ECT assay (ecarin clotting time) and the Heptest® assay [see U.S. Pat. Nos. 4,946,775, 4,756,884, 4,861,712, 5,059,525, 5,110,727 and 5,300,779 and Thrombosis and Hemorrhage (op. cit.), and Kandrotas, R. J., Heparin Pharmokinetics and Pharmacodynamics, Clin. Pharmacokinet., vol. 22, 1992, pages 359-374].

The products obtained via the synthesis methods of this invention may be characterized by any number of methods well known to one skilled in the art. In one embodiment, the products are characterized via proton and carbon $^{13}$NMR analysis. In another embodiment, products may be analyzed by capillary HPLC-ESI-TOF-MS, via methods exemplified herein.

In another embodiment, the molecular weight of the products of the synthesis can be tailored at any stage by standard chemical or enzymatic cleavage techniques which have been utilized in similar fashion to produce low molecular weight compounds, as is well known to one skilled in the art. Such tailoring may be accomplished following the synthesis methods/processes of the present invention, or may occur in a single reaction mixture, such as is outlined herein, with reaction mixtures comprising endoglycosidases, providing depolymerized acceptor saccharides. It is to be understood that any of these embodiments are to be considered as part of this invention.

In one embodiment, low molecular weight compounds may be generated via enzymatic digestion of unfractionated or partially fractionated product, such as, for example, via heparatinase or glucuronidase cleavage of the sulfated heparosan polysaccharides of this invention. In one embodiment, low molecular weight compounds are generated via enzymatic cleavage of the heparosan polysaccharide represented by the structure of formula V.

According to this aspect of the invention, the lower molecular mass derivatives of the compound of Formula V obtained may include, in one embodiment, ΔU-GlcNS3S6S, or in another embodiment, the derivative is ΔU-GlcNAc6S-GlcA-GlcNS3S6S, or in another embodiment, the derivative is ΔU-GlcNAc6S-GlcA-GlcNS3S, or in another embodiment, the derivative is ΔU-GlcNS6S-GlcA-GlcNS3S6S, with structures of which are represented by the formulas below:

ΔU-GlcNS3S6S

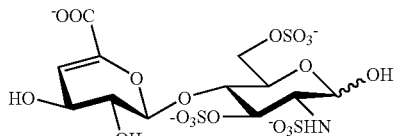

ΔU-GlcNAc6S-GlcA-GlcNS3S6S

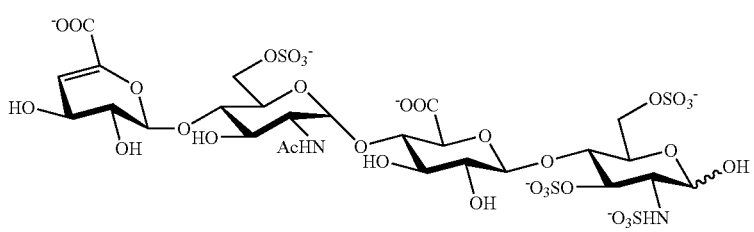

-continued

ΔU-GlcNAc6S-GlcA-GlcNS3S

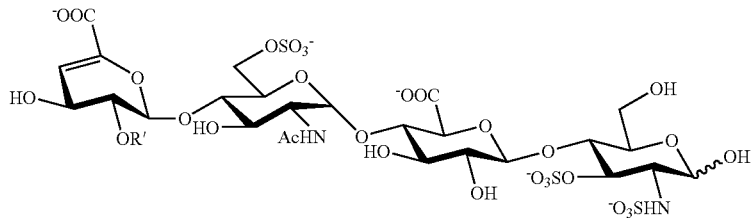

ΔU-GlcNS6S-GlcA-GlcNS3S6S

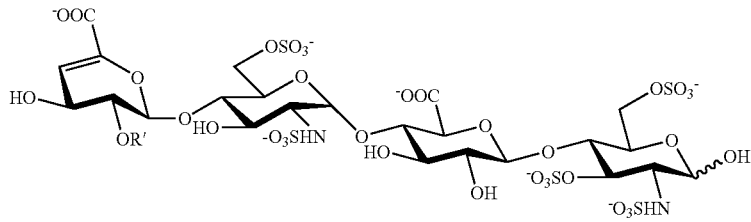

In one embodiment, the enzymes used to generate low molecular weight compounds of the sulfated heparosan polysaccharides obtained via the methods/processes and in the reaction mixtures described herein may be derived from any source, such as native, or in another embodiment, recombinant enzymes, such as for example, heparatinases as disclosed in U.S. Pat. No. 5,290,695. In one embodiment, Heparitinase I is utilized. In another embodiment, Heparitinase II is utilized. In another embodiment, Heparitinase III is utilized. In another embodiment, any heparanase or endoglucuronidase may be utilized to cleave the polymers, and comprise additional embodiments of the invention. In another embodiment, cleavage may be accomplished via the use of nitrous acid/borohydride reduction, via methods well known to one skilled in the art.

In one embodiment, when sufficient digestion of the unfractionated or partially fractionated sulfated heparosan polysaccharides has taken place, the enzyme is inactivated. Inactivation of the enzyme can be effected in any one of a plurality of techniques employed in the art for enzyme inactivation, including, but not limited to, heat inactivation, dilution, e.g., by dialysis, exposure to extreme pH followed, for example, by neutralization, and the like. The time required for sufficient digestion of the unfractionated or partially fractionated sulfated heparosan polysaccharides will depend on several factors, including, but not limited to, active enzyme concentration, temperature, pH and solutes other than the enzyme and substrate. One ordinarily skilled in the art would know how to modify these factors so as to obtain controlled and repetitive performance.

It will be appreciated by one ordinarily skilled in the art that the digestive enzyme can be bound to a solid matrix and that the time of digestion of the unfractionated or partially fractionated product can thus by controlled by controlling the exposure time of the unfractionated or partially fractionated sulfated heparosan polysaccharides to the solid matrix.

Monitoring the digestion reaction according to the present invention can be effected by periodic sampling and one of a plurality of known techniques, including, but not limited to, high performance liquid chromatography, conventional chromatography, mass spectroscopy, gel electrophoresis and the lice. Thus, when sufficient digestion of the unfractionated or partially fractionated sulfated heparosan polysaccharides has taken place as determined by any one of the above techniques the enzyme is inactivated, so as to control the molecular mass of the resulting digestion products.

According to another embodiment of the present invention, the sulfated heparosan polysaccharides with a relatively low molecular mass generated following sufficient digestion with the enzymes, as described, is precipitated, e.g., by the addition of ethanol and salt and appropriate centrifugation.

In another, the sulfated heparosan polysaccharides with a relatively low molecular mass generated following sufficient digestion with an enzyme as described, is size fractionated and a low molecular weight sulfated heparosan polysaccharides of a specific molecular mass range is collected. Size fractionation can be effected by any one of a variety of techniques known in the art, including, but not limited to, high performance liquid chromatography, conventional chromatography, mass spectroscopy, gel electrophoresis, differential filtration, differential centrifugation, differential dialysis and the like.

Sulfation may also follow cleavage of the sulfated heparosan polysaccharides to compounds with relatively low molecular mass, in one embodiment. It is to be understood that multiple rounds of cycling and cleavage may occur in the reaction mixture, which in one embodiment provides for an array of sulfated heparosan polysaccharide products, and is to be considered as part of this invention.

In another embodiment, this invention provides a reaction mixture for producing a N-sulfate derivative of non-sulfated N-acetyl heparosan (HS) polysaccharide product, wherein the reaction mixture comprises: an acceptor non-sulfated N-acetyl heparosan (HS) polysachalide, a 3'-phosphoadenosine 5'-phosphosulfate (PAPS) sulfate donor, an N-deacetylase-N-sulfotransferase that catalyzes sulfate transfer from the PAPS donor to the acceptor polysaccharide, generating an iduronic acid-enriched heparosan polysaccharide, a glucuronosyl C-5 epimerase that catalyzes conversion of the acceptor heparosan polysachalide to its epimer, following N-sulfation; a p-nitrophenyl sulfate donor, an aryl sulfatase that catalyzes sulfate group cleavage from p-nitrophenyl sulfate, wherein said cleaved sulfate group serves to regenerate PAPS, a 6-O sulfotransferase (6-OST) that catalyzes O-sulfation on carbon 6 of the acceptor polysaccharide, and a 3-O sulfotransferase (3-OST), that catalyzes O-sulfation on carbon 3 of the acceptor polysaccharide.

In another embodiment, additional glycosaminoglycans are synthesized via the methods/processes of this invention. According to this aspect of the invention, reaction mixtures as described hereinabove are produced, wherein the sulfotransferase utilized may comprise a chondroitin 6/keratin 6 sulfate sulforansferase, or in another embodiment, the a galactosylceramide 3'-sulforansferase, or in another embodiment, a HNK-1 sulfotransferase. The acceptor saccharide, according to this aspect of the invention, in one embodiment, will be the corresponding substrate for sulfation by the respective sulfotransferases. In one embodiment the acceptor saccharide is a chondroitin, a dermatan, a keratin or a hyaluronic acid.

It is to be understood that the method/process, according to this aspect of the invention, includes all embodiments herein described, for the generation of novel glycosaminoglycans.

The following are meant to provide materials, methods, and examples for illustrative purposes as a means of practicing/executing the present invention, and are not intended to be limiting.

EXAMPLES

Example 1

Effective Coupling of Enzyme Activities for Synthesis of an N-Sulfated N-Deacetylated Polysaccharide Materials and Methods Reagents HS precursor polysaccharide was prepared from E. coli K5 strain (W. F. Vann, M. A. Schmidt, B. Jann, K. Jann, Eur J Biochem 116, 359-64 (1981)). Heparan Sulfate C-5 epimerase, 3-OST1,6-OST2a, and NDST2 sulfotransferases were all cloned and expressed in a baculovirus system [A. Orellana, C. B. Hirschberg, Z. Wei, S. J. Swiedler, M. Ishihara, J Biol Chem 269, 2270-6 (1994); J. Li et al., J Biol Chem 272, 28158-63 (1997); H. Habuchi et al., J Biol Chem 275, 2859-68 (2000); J. Liu, N. W. Shworak, L. M. S. Flitze, J. M. Edelberg, R. D. Rosenberg, Journal of Biological Chemistry 271, 27072-27082 (1996); and N. W. Shworak et al., Journal of Biological Chemistry 274, 5170-5184 (1999)]. [$^{35}$S] PAPS and [34S] pAPS were prepared as reported earlier, whereas [$^{32}$S] PAPS was purchased from Calbiochem. All chemicals were purchased from Sigma. ATIII and Factor Xa were from Haematologic Technologies Inc. Chromogenic substrate S-2765 was from Chromogenix. Heparitinase L II and III were obtained from Seikagagu. APS kinase was a generous gift from Professor I. H. Segel (Univ. of California, Davis).

cDNA Cloning of Human Glucuronyl C5 Epimerase

A cDNA clone coding for human C5 epimerase was isolated from a human fetal brain cDNA panel (origene, Rockville, Md.) by screening with PCR primers spanning nucleotides 7-157 of the coding region. A donor plasmid for the preparation of recombinant baculovirus expressing a soluble form of the epimerase was constructed in pFastBac HT plasmid (Gibco, Grand Island, N.Y.) modified by the insertion of honeybee melittin signal peptide ahead of the histidine tag. The construction employed a synthetic oligonucleotide adapter that also encoded amino acids 35-44 of the epimerase and two restriction fragments isolated from the cDNA clone (TaqI to EcoRI and EcoRI to SacI) that incorporate the rest of the epimerase coding region.

Baculovirus Expression and Purification of Glucuronyl C5 Epimerase

Human glucuronyl C5 epimerase recombinant baculovirus was prepared using the donor and the Bac-to-Bac baculovirus expression system (Life Technologies, Inc. Grand Island, N.Y.) according to the manufacturer's protocol, except that recombinant bacmid DNA was purified using an endotoxin-free plasmid purification kit (Qiagen, Inc. Valencia, Calif.) and transfection of Sf9 cells was scaled up to employ 15 μg of bacmid DNA and $2.5 \times 10^7$ exponentially growing cells in four 100-mm dishes. Medium containing recombinant baculovirus was harvested at 3 days post-transfection and amplified twice for about 65 hours each on Sf9 cells. The resulting high-titer viral stock was stored in aliquots (0.75 ml) sufficient to infect $3.5 \times 10^8$ cells, as determined by Western blotting of medium from infected cells using (his)4 antibody (Qiagen). Infected cells were plated in ten 150 mm dishes and incubated at 26° C. for 90-96 hours. The pooled medium was centrifuged at 400×g, adjusted to 10 mM in HEPES, titrated to pH 7.4, chilled on ice for 30 minutes and centrifuged at 16,000×g. The clarified pool diluted in half with 10 mM HEPES, pH 7.4, made 1 mM in PMSF, and applied to an 8 ml column of ToyoPearl AF heparin 650M (TOSOHAAS, Montgomeryville, Pa.). The column was washed with 40 ml of HCG 50 (10 mM HEPES, pH 7.4, 2% glycerol, 0.6% CHAPS, 50 mM NaCl) and eluted with an 80 ml linear gradient of 50 to 600 mM NaCl in HCG. Aliquots of selected 1 ml fractions were analyzed by western blotting for the presence of the histidine tag, adjusted to 500 mM in NaCl, 10 mM in imidazole and concentrated an Amicon YM-10 membrane (Amicon, Bedford, Mass.) to about 3 ml.

Enzymatic Modification with Recombinant Enzymes: NDST2, C5 Epi, 6-OST2a, and 3-OST1

The labeling 2× buffer contains 50 mM MES (pH 7.0), 1% (W/V) triton X-100, 5 mM $MgCl_2$, 5 mM $MnCl_2$, 2.5 mM $CaCl_2$, 0.075 mg/ml protamine chloride, 1.5 mg/ml BSA or 25 mM HEPES, 40 mM $CaCl_2$, pH 6.5. For a 2500 μl reaction, the following were assembled: polysaccharide (final concentration was 1 mM equivalent of unmodified disaccharide), 1250 μl of 2× buffer, 50 ng of the expressed sulfotransferase or epimerase, [$^{35}$S] 3'-phosphoadenosine 5'-phosphosulfate (PAPS) ($1.0 \times 10^7$ cpm) or [$^{32}$S]PAPS (final concentration of 20 μM), and the appropriate amount of water. The reaction was incubated at 37° C. for 12 hours, then diluted to 5 ml with DEAE wash buffer and purified on DEAE column. Alternatively, the reaction was stopped by heating at 70° C. and the reaction mixture was centrifuged at 10,000 g for 3 min and the supernatant was used for gel mobility shift analysis. Modified polysaccharide was digested with heparitinases I, II and III and was analyzed by capillary HPLC-ESI-TOF-MS.

Results

A non-sulfated N-acetyl heparosan (HS) polysaccharide, the compound represented by the structure of Formula II (FIG. 1, step 1) was isolated from the E. coli strain K5, which resembles the unmodified nascent HS chain, and was used as a starting material. Synthesis of an N-sulfated polysaccharide enriched with iduronic acid (represented by the structure of Formula V) was catalyzed by N-deacetylase-N-sulfotransferase (NDST) and C-5 epimerase (step 2). These two initial modifications were the essential gateway for subsequent enzymatic modifications.

A single protein catalyzes both N-deacetylation and N-sulfation. These two reactions are tightly coupled in vivo, since free glucosamine residues are rarely found in HS and Heparin, even though each activity can be studied separately in vitro. The NDST enzyme exists as four isoforms in humans. The NDST2 isoform was utilized to selectively N-deacetylate and N-sulfate glucosamine units.

The deacetylation and N-sulfation of the K5 polysaccharide was carried out in the presence of the Heparan Sulfate C-5 epimerase enzyme, as well, in order to generate the iduronic acid-enriched polysacchalide (the compound represented by the structure of Formula IV).

The stereochemical nature at the C-5 carbon of uronic acid is reversed during transformation of the compound represented by the structure of Formula II to the compound represented by the structure of Formula V of FIG. 1. Epimerization proceeds on condition that uronic acid residues are located at the reducing side of N-sulfated glucosamine residues. Epimerization will not proceed should the uronic acid be O-sulfated or be adjacent to O-sulfated glucosamine residues or N-acetylglucosamine units. The stereochemical constraint imposed indicates that epimerization occurs immediately following N-deacetylation and N-sulfation but prior to O-sulfation.

The sterochemical constraint was exploited in the synthetic strategy of the present invention. NDST2 and C5 epimerase activity were coupled in order to prepare in a single step N-sulfated polysaccharide (the compound represented by the structure of Formula V) containing both glucuronic and iduronic acid, without 2-O sulfation.

The final step (step 3) in the synthesis of the N-deacetylate N-sulfate derivatives of non-sulfated N-acetyl heparosan (HS) polysaccharides (the compound represented by the structure of Formula I) was catalyzed by combined activity of 6-O sulfotransferase (6-OST) and 3-O sulfotransferase (3-OST). There are three heparan sulfate 6-O sulfotransferase isoforms: 6-OST1, 6-OST2 (6-OST2a and 6-OST2b are two splice variants) and 6-OST3 (15). Though all three isoforms sulfate CDSNS-Heparin equally well, N-sulfo-heparosan was preferentially sulfated in the following order: 6-OST2 sulfated to a greater extent than 6-OST3, which sulfated to a much greater extent as compared to 6-OST1. The 6-OST2a isoform was utilized to catalyze the 6-O sulfation of glucosamine units in Formula V.

6-O sulfation was coupled with 3-O sulfation, which is catalyzed by 3-OST1 sulfotransferase. There are as many as five isoforms of heparan sulfate 3-O sulfotransferases, namely 3-OST1, 3-OST2, 3-OST3, 3-OST4, and 3-OST5. 3-OST1 has been shown primarily responsible for generating the anticoagulant heparan. 3-OST1 generally acts on glucosamine units flanked by the reducing side of glucuronic acid (GlcUA) and the non-reducing side of iduronic acid (IdoA) to generate anti-thrombin (AT)III antibody binding structures containing GlcUA-GlcNS$_3$S and GlcUA-GlcNS$_3$S$_6$S. Coupling of 6-O sulfation and 3-O sulfation was conducted in order to determine whether this coupling would shorten the time required for total synthesis of the compound represented by the structure of Formula IV, which was readily accomplished.

Example 2

High-Yield Synthesis of an N-Sulfated N-Deacetylated Polysaccharide Via Coupling of Enzyme Activities and PAPS Regeneration Materials and Methods:

All materials and methods were as described in Example 1, with the following exceptions:

Reagents:

Aryl sulfatase was provided by C. H. Wong.

Enzymatic Modification with Recombinant Enzymes: NDST2, C5 Epi, aryl sulfatase, 6-OST2a, and 3-OST1

The labeling 2× buffer contains 50 mM MES (pH 7.0), 0.001% (W/V) triton X-100, 5 mM MgCl$_2$, 5 mM MnCl$_2$, 2.5 mM CaCl$_2$, 0.25 mg/ml BSA or 25 mM HEPES, 40 mM CaCl$_2$, pH 6.5 with or without p40. For a 2500 μl reaction, the following were assembled: polysaccharide (final concentration was 1 mM equivalent of unmodified disaccharide), 1250 μl of 2× buffer, 50 ng of the expressed sulfotransferase or epimerase, p-nitrophenyl sulfate (final concentration of 40 mM), 50 ng of aryl sulfatase, [$^{35}$S] 3'-phosphoadenosine 5'-phosphosulfate (PAPS) (1.0×10$^7$ cpm) or [$^{32}$S] PAPS (final concentration of 20 μM), and the appropriate amount of water. The reaction was incubated at 37° C. for 12 hours, then diluted to 5 ml with DEAE wash buffer and purified on DEAE column. Alternatively, the reaction was stopped by heating at 70° C. and the reaction mixture was centrifuged at 10,000 g for 3 min and the supernatant was used for gel mobility shift analysis. Modified polysaccharide was digested with heparitinases I, II and III and was analyzed by capillary HPLC-ESI-TOF-MS.

Results

K5 non-sulfated N-acetyl heparosan (HS) polysaccharide was utilized as a starting material, as in Example 1. In addition to the use of the NDST2 isoform to selectively N-deacetylate and N-sulfate glucosamine units, P-nitrophenylsulfate and aryl sulfatase were included in the reaction mix.

3'-phosphoadenosine 5'-phosphosulfate (PAPS) hydrolysis provided free sulfate groups, utilized for N-sulfation of glucosamine units via NDST, following which, highly reactive PAP was generated. Because of the addition of excess p-nitrophenyl sulfate in the reaction mix and the presence of aryl sulfatase, PAPS was then regenerated, leaving the reaction product, P-nitrophenol.

The reaction proceeded as in Example 1, with epimerization of the C-5 carbon accomplished via the activity of epimerase, as described. Thus coupling of the activity of the 3 enzymes, NDST, aryl sulfatase and C5 epimerase prepared the N-sulfated polysaccharide in a single step, while concurrently regenerating PAPS, via the presence of excess p-nitrophenyl sulfate.

Figure 2:
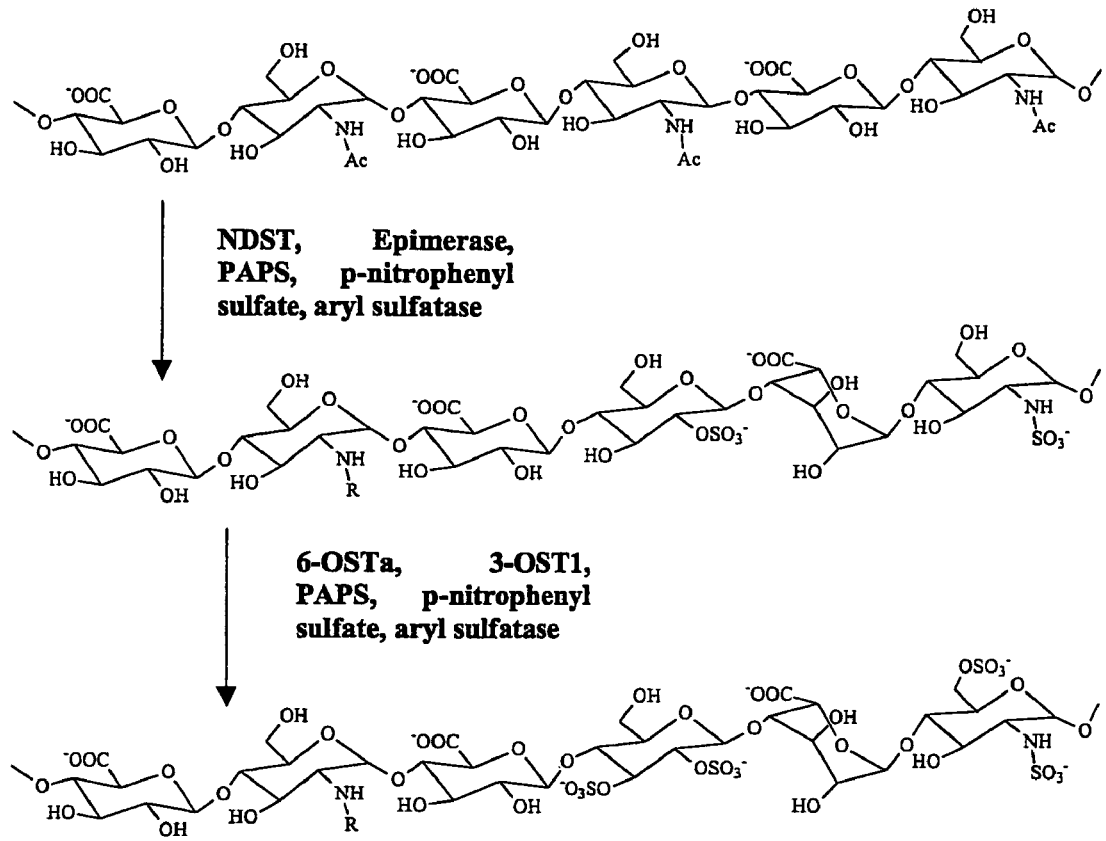
FIG. 2 schematically depicts the enzymatic synthesis of N-deacetylate N-sulfate derivatives of non-sulfated N-acetyl heparosan (HS) polysaccharides, via a method regenerating PAPS (inset).
Figure 2:
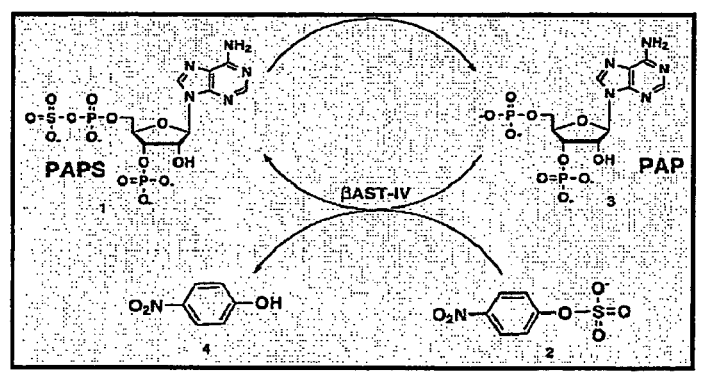

The combined activity of 6-O sulfotransferase (6-OST) and 3-O sulfotransferase (3-OST) preferentially sulfated the compound to yield the product represented by the structure of Formula IV, as in Example 1, schematically depicted in FIG. 2. The compound obtained was comparable to that obtained via the method of Example 1.

Sulfotransferase activity is inhibited in the presence of high PAPS concentration. NDST activity results in the incorporation of free sulfate (PAPS hydrolysis) within the polysaccharide. PAPS regeneration via incorporation of sulfate donated by p-nitrophenyl sulfate (due to aryl sulfatase activity) provides for greater product yields, and greater efficiency in sulfating the polysaccharide. Further, the cyclic nature of PAPS hydrolysis and regeneration results in diminished overall free sulfate concentration, which in turn facilitates greater sulfotransferase activity and efficiency.

Example 3

Product Yields of N-Deacetylate N-Sulfate Derivatives of Non-Sulfated N-Acetyl Heparosan (HS) Polysaccharide Materials and Methods Digestion of Polysaccharides with Heparitinase I, II, and III Polysaccharides were digested with 1 mU of HepI, II and III in a total volume of 100 μl of 40 mM Ammonium acetate containing 1 mM Calcium chloride buffer (pH 7.0) at 37° C. overnight.

Flow Injection Capillary Liquid Chromatography

An Ultimate capillary HPLC workstation (Dionex, Sunnyvale, USA) was used for microseparation. UltiChrom software was used in data acquisition and analysis. A gradient elution was performed, using a binary solvent system composed of water (eluent A) and 70% aqueous methanol (eluent B), both containing 8 mM acetic acid and 5 mM dibutylamine as an ion-pairing agent. HPLC separations were performed on a 0.3 mm×250 mm C18 polymeric silica column (Vydac, Hesperia, USA). The column temperature was maintained at 25° C. and the flow rate was set to 5 mL min-1. Sample volumes of 6.3 mL were injected. The chromatographic conditions were optimized for resolution of disaccharides. In brief, non-sulfated disaccharide was eluted with 100% A, single sulfated disaccharides were eluted with 10% B, isocratic elution with 20% B for double sulfated disaccharides, followed by isocratic elution with 35% B for triple sulfated disaccharide. The column was washed and equilibrated by further elution with 100% B for 10 min, returning to 100% A for 10 min at the end of the run. The absorbance of the column eluate was monitored at 232 nm.

Mass Spectrometry

Mass spectra were acquired on a Mariner BioSpectrometry Workstation ESI tilne-of-flight mass spectrometer (PerSeptive Biosystems, Framingham, Mass.). In the negative-ion mode, the instrument was calibrated with bis-trifluoromethyl benzoic acid, heptadecafluorononanoic acid, and perfluorotetradecanoic acid. Nitrogen was used as a desolvation gas as well as a nebulizer. Conditions for ESI-MS were as follows: nebulizer flow 0.75 L/min, nozzle temperature 140° C., drying gas ($N_2$) flow 1.2 L/min, spray tip potential 2.8 kV, nozzle potential 70 V, and skimmer potential 12 V. Negative ion spectra were generated by scanning the range of m/z 40-2000. During analyses, the indicated vacuum was $1.9 \times 10^{-6}$ Torr.

Results

Figure 3:
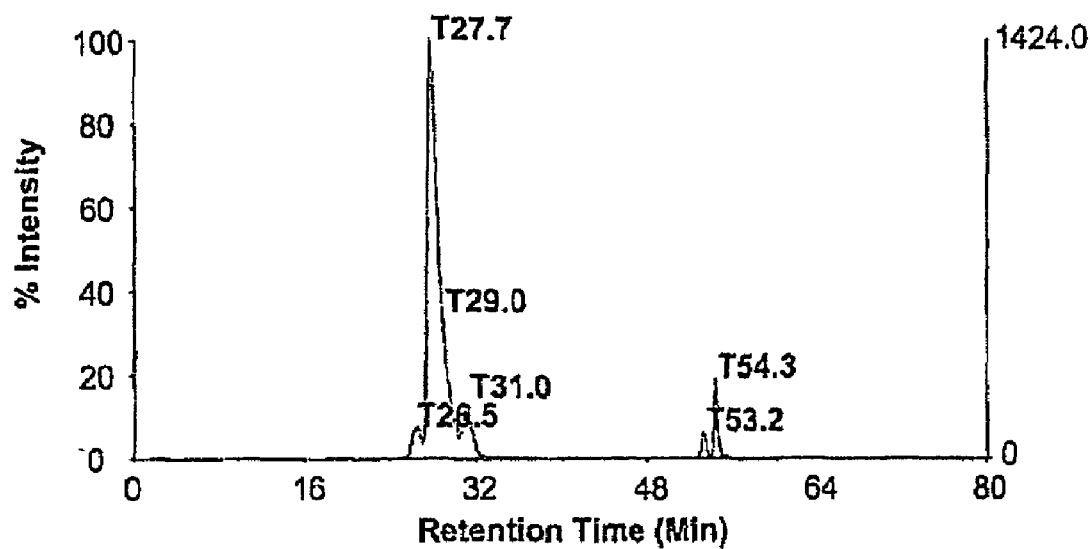
FIG. 3 demonstrates the results of a disaccharide analysis of N-sulfated heparosan by LC-MS.
Figure 3:
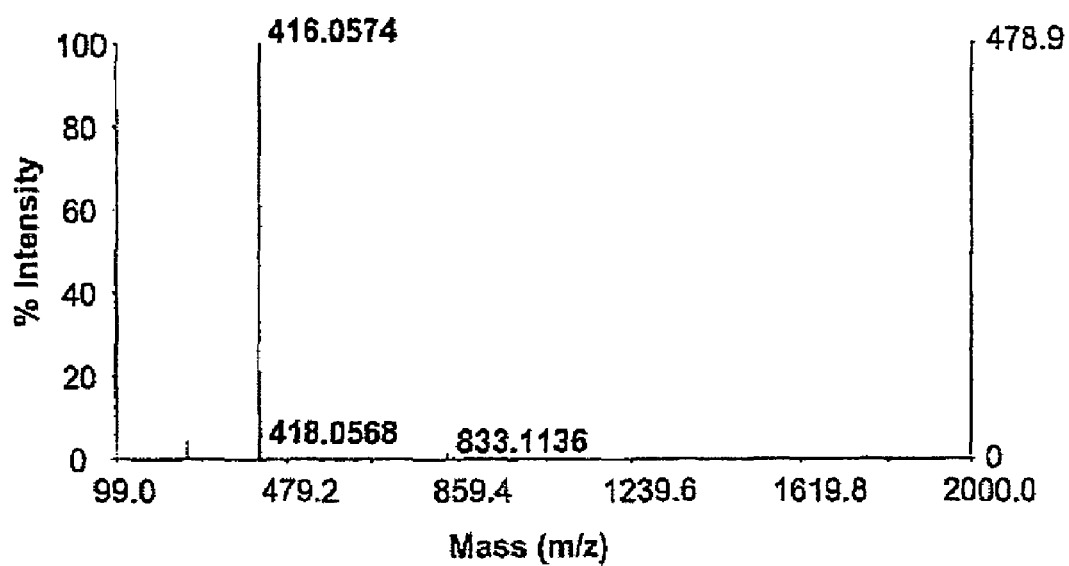

The compound of Formula IV was subjected to capillary liquid chromatography coupled to electro-spray mass spectrometry (LC/MS) analysis, in order to determine the product composition and yield [FIG. 3]. The LC/MS analysis of the N-sulfated polysaccharide product and hence it should have showed one major peak, corresponding to molecular ion 416.0574 [M−1H]-1.

While product composition is comparable, regardless of whether the synthesis method employed PAPS regeneration or not, a difference in product yield was evident. LC/MS analysis of products following a synthesis method facilitating PAPS regeneration resulted in N-sulfated disaccharide production which accounts for at least roughly 90% modification catalyzed by NDST2, whereas the absence of PAPS regeneration provided only roughly 75% conversion. Thus, the regeneration of PAPS resulted in greater NDST efficiency.

Example 4

High-Yield Synthesis of an N-Sulfated N-Deacetylated Polysaccharide Via Coupling of Enzyme Activities and PAPS Regeneration Materials and Methods:

All materials and methods were as described in Examples 1 and 2, with the following exception: p-nitrophenyl sulfate was purchased from Sigma.

Enzymatic Modification with Recombinant Enzymes: NDST2, C5 Epi, aryl sulfatase, 6-OST2a, and 3-OST1

The labeling 2× buffer contains 50 mM MES (pH 7.0), 0.001% (W/V) triton X-100, 5 mM $MgCl_2$, 5 mM $MnCl_2$, 2.5 mM $CaCl_2$, 0.25 mg/ml BSA or 25 mM HEPES, 40 mM $CaCl_2$, pH 6.5 with or without p40. For a 2500 µl reaction, the following were assembled: polysaccharide (final concentration was 1 mM equivalent of unmodified disaccharide), 1250 µl of 2× buffer, 50 ng of the expressed sulfotransferase or epimerase, p-nitrophenyl sulfate (final concentration of 40 mM), 50 ng of aryl sulfatase, [$^{35}$S] 3'-phosphoadenosine 5'-phosphosulfate (PAPS) ($1.0 \times 10^7$ cpm) or [$^{32}$S] PAPS (final concentration of 20 µM), and the appropriate amount of water. The reaction was incubated at 37° C. for 12 hours, then diluted to 5 ml with DEAE wash buffer and purified on DEAE column. Alternatively, the reaction was stopped by heating at 70° C. and the reaction mixture was centrifuged at 10,000 g for 3 min and the supernatant was used for gel mobility shift analysis. Modified polysaccharide was digested with heparitinases I, II and II and was analyzed by capillary HPLC-ESI-TOF-MS.

Results

K5 non-sulfated N-acetyl heparosan (HS) polysaccharide was utilized as a starting material, as in Example 1. In addition to the use of the NDST2 isoform to selectively N-deacetylate and N-sulfate glucosamine units, P-nitrophenylsulfate and aryl sulfatase were included in the reaction mix.

3'-phosphoadenosine 5'-phosphosulfate (PAPS) hydrolysis provided free sulfate groups, utilized for N-sulfation of glucosamine units via NDST, following which, highly reactive PAP was generated. Because of the addition of excess p-nitrophenyl sulfate in the reaction mix and the presence of aryl sulfatase, PAPS was then regenerated, leaving the reaction product, P-nitrophenol.

The reaction proceeded as in Example 1, with epimerization of the C-5 carbon accomplished via the activity of epimerase, as described. Thus coupling of the activity of the 3 enzymes, NDST, aryl sulfatase and C5 epimerase prepared the N-sulfated polysacchalide in a single step, while concurrently regenerating PAPS, via the presence of excess p-nitrophenyl sulfate.

The combined activity of 6-O sulfotransferase (6-OST) and 3-O sulfotransferase (3-OST) preferentially sulfated the compound to yield the product represented by the structure of Formula IV, as in Example 1, schematically depicted in FIG. 2. The compound obtained was comparable to that obtained via the method of Example 1.

Sulfotransferase activity is inhibited in the presence of high sulfate concentration. NDST activity results in the incorporation of free sulfate (PAPS hydrolysis) within the polysaccharide. PAPS regeneration via incorporation of sulfate donated by p-nitrophenyl sulfate (due to aryl sulfatase activity) provides for greater product yields, and greater efficiency in sulfating the polysaccharide. Further, the cyclic nature of PAPS hydrolysis and regeneration results in diminished overall free sulfate concentration, which in turn facilitates greater sulfotransferase activity and efficiency.

Example 5

Effective Coupling of Enzyme Activities for Synthesis of a Sulfated Depolymerized Heparosan Polysaccharide Materials and Methods Reagents Precursor polysaccharide is prepared from *E. coli*, K5 strain. 6-OST2a, aryl sulfatase and $\Delta^{4,5}$-Glucuronidase are provided by Yoshida. Radioisotope-labeled PAPS is prepared as described hereinabove.

Enzymatic Modification With Recombinant Enzymes: 6-OST2a, aryl sulfatase and D 4,5-Glucuronidase:

The labeling 2× buffer contains 50 mM MES (pH 7.0), 0.001% (W/V) triton X-100, 5 mM MgCl$_2$, 5 mM MnCl$_2$, 2.5 mM CaCl$_2$, 0.25 mg/ml BSA or 25 mM HEPES, 40 mM CaCl$_2$, pH 6.5 with or without p40. For a 2500 µl reaction, the following are assembled: polysaccharide (final concentration is 1 mM equivalent of unmodified disaccharide), 1250 µl of 2× buffer, 50 ng of the expressed enzyme, p-nitrophenyl sulfate (final concentration of 40 mM), 50 ng of aryl sulfatase, [$^{35}$S] 3'-phosphoadenosine 5'-phosphosulfate (PAPS) (1.0× 10$^7$ cpm) or [$^{32}$S] PAPS (final concentration of 20 µM), and the appropriate amount of water. The reaction is incubated at 37° C. for 12 hours, then diluted to 5 ml with DEAE wash buffer and purified on DEAE column. Alternatively, the reaction is stopped by heating at 70° C. and the reaction mixture is centrifuged at 10,000 g for 3 minutes.

Results

Figure 4:
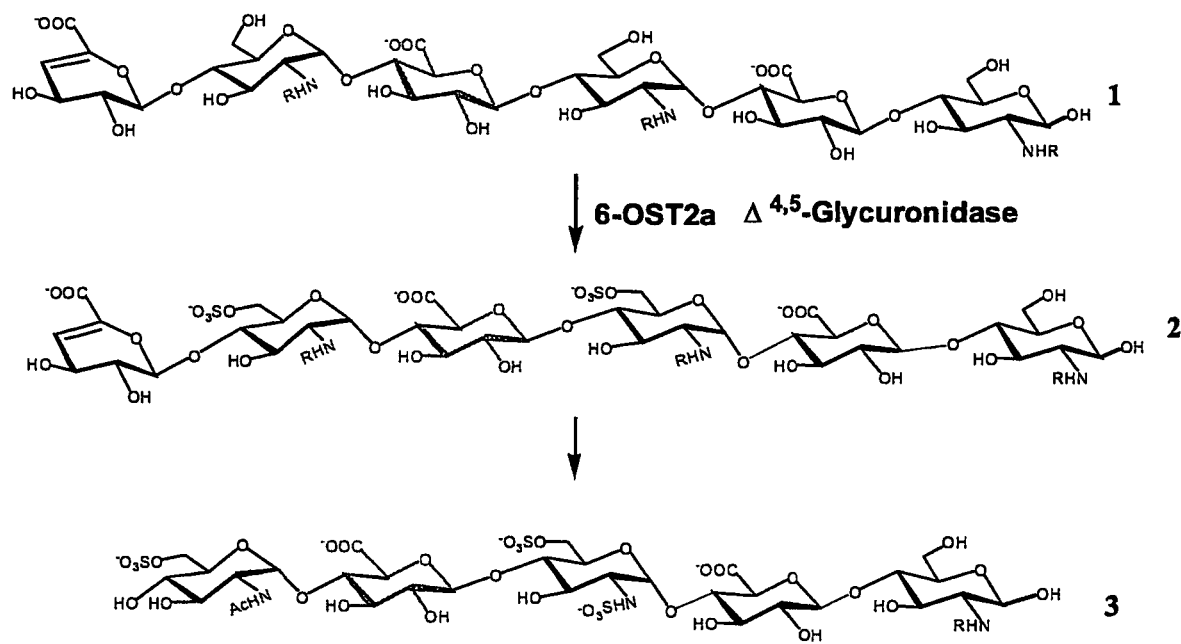
FIG. 4 schematically depicts a reaction scheme for the synthesis of depolymerized heparosan pentasaccharide. The pentasaccharide is obtained following the incubation of a heparosan polysaccharide with 6OST2a for sulfation, and p-nitrophenylsulfate and aryl sulfatase for regenerating PAPS, as described, and $\Delta^{4,5}$-Glucuronidase for the generation of the pentasaccharide.

K5 non-sulfated heparosan (HS) polysaccharide is utilized as a starting material as in Example 1. In addition to the use of 6OST2a to selectively O-sulfate the hexasaccharide, P-nitrophenylsulfate and aryl sulfatase are included in the reaction mix, to ensure, as above, PAPS regeneration for enhanced product yield. The inclusion of Δ$^{4,5}$-Glucuronidase provides for the generation of a depolymerized heparosan polysaccharide, as depicted in FIG. 4.

Example 6

Effective Coupling of Enzyme Activities for Synthesis of a Sulfated Depolymerized Heparosan Polysaccharide Materials and Methods Reagents Precursor polysaccharide is prepared, and NDST2, epimerase, Heparitinase I, aryl sulfatase and Δ$^{4,5}$-Glucuronidase are obtained, as described above. Radioisotope-labeled PAPS is prepared as described hereinabove.

Enzymatic Modification with Recombinant Enzymes: 6-OST2a, aryl sulfatase and D 4,5-Glucuronidase:

The labeling 2× buffer contains 50 mM MES (pH 7.0), 0.001% (W/V) triton X-100, 5 mM MgCl$_2$, 5 mM MnCl$_2$, 2.5 mM CaCl$_2$, 0.25 mg/ml BSA or 25 mM HEPES, 40 mM CaCl$_2$, pH 6.5 with or without p40. For a 2500 µl reaction, the following are assembled: polysaccharide (final concentration is 1 mM equivalent of unmodified disaccharide), 1250 µl of 2× buffer, 50 ng of the expressed enzymes, p-nitrophenyl sulfate (final concentration of 40 mM), 50 ng of aryl sulfatase, [$^{35}$S] 3'-phosphoadenosine 5'-phosphosulfate (PAPS) (1.0× 10$^7$ cpm) or [$^{32}$S] PAPS (final concentration of 20 µM), and the appropriate amount of water. The reaction is incubated at 37° C. for 12 hours, then diluted to 5 ml with DEAE wash buffer and purified on DEAE column. Alternatively, the reaction is stopped by heating at 70° C. and the reaction mixture is centrifuged at 10,000 g for 3 minutes.

Results

Figure 5:
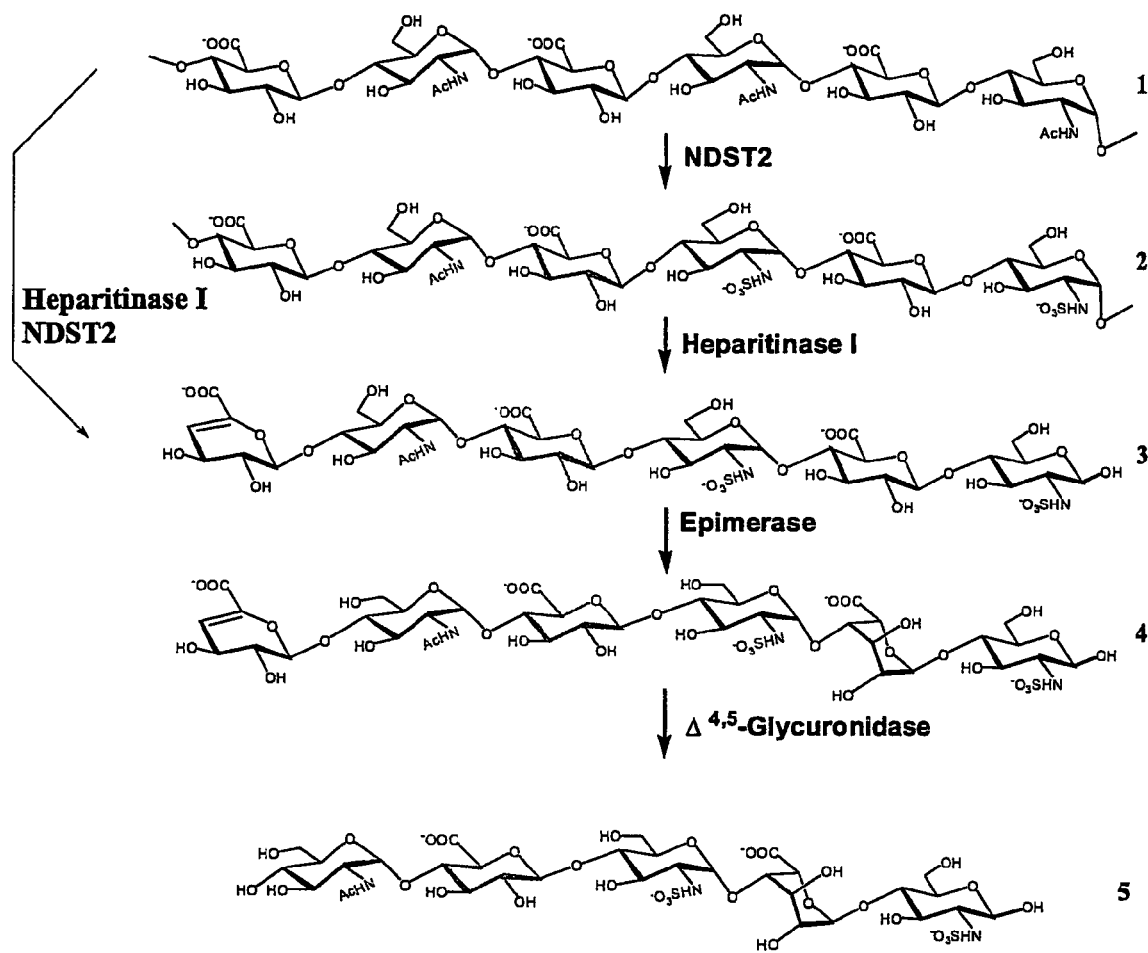
FIG. 5 depicts a reaction scheme for the synthesis of an epimerically enriched, depolymerized heparosan pentasaccharide. A hexasaccharide is obtained following the incubation of a heparosan polysaccharide with NDST2 to selectively N-deacetylate and N-sulfate the polysaccharide, and Heparatinase I to generate the hexasaccharide, while p-nitrophenylsulfate and aryl sulfatase regenerate PAPS, as described. The epimerase and $\Delta^{4,5}$-Glucuronidase provide for the generation of the depolymerized heparosan pentasaccharide, which is an epimer of the compound represented by structure 3.

K5 non-sulfated heparosan (HS) polysaccharide is utilized as a starting material. In addition to the use of NDST2 to selectively N-deacetylate and N-sulfate the hexasaccharide, Heparitinase is utilized to generate the hexasaccharide, as schematically depicted in FIG. 5. The inclusion of an epimerase and Δ$^{4,5}$-Glucuronidase provides for the generation of the depolymerized heparosan pentasaccharide, which is an epimer of the compound represented by structure 3 in FIG. 5. P-nitrophenylsulfate and aryl sulfatase are included in the reaction mix, to ensure, as above, PAPS regeneration for enhanced product yield.

Figure 6:
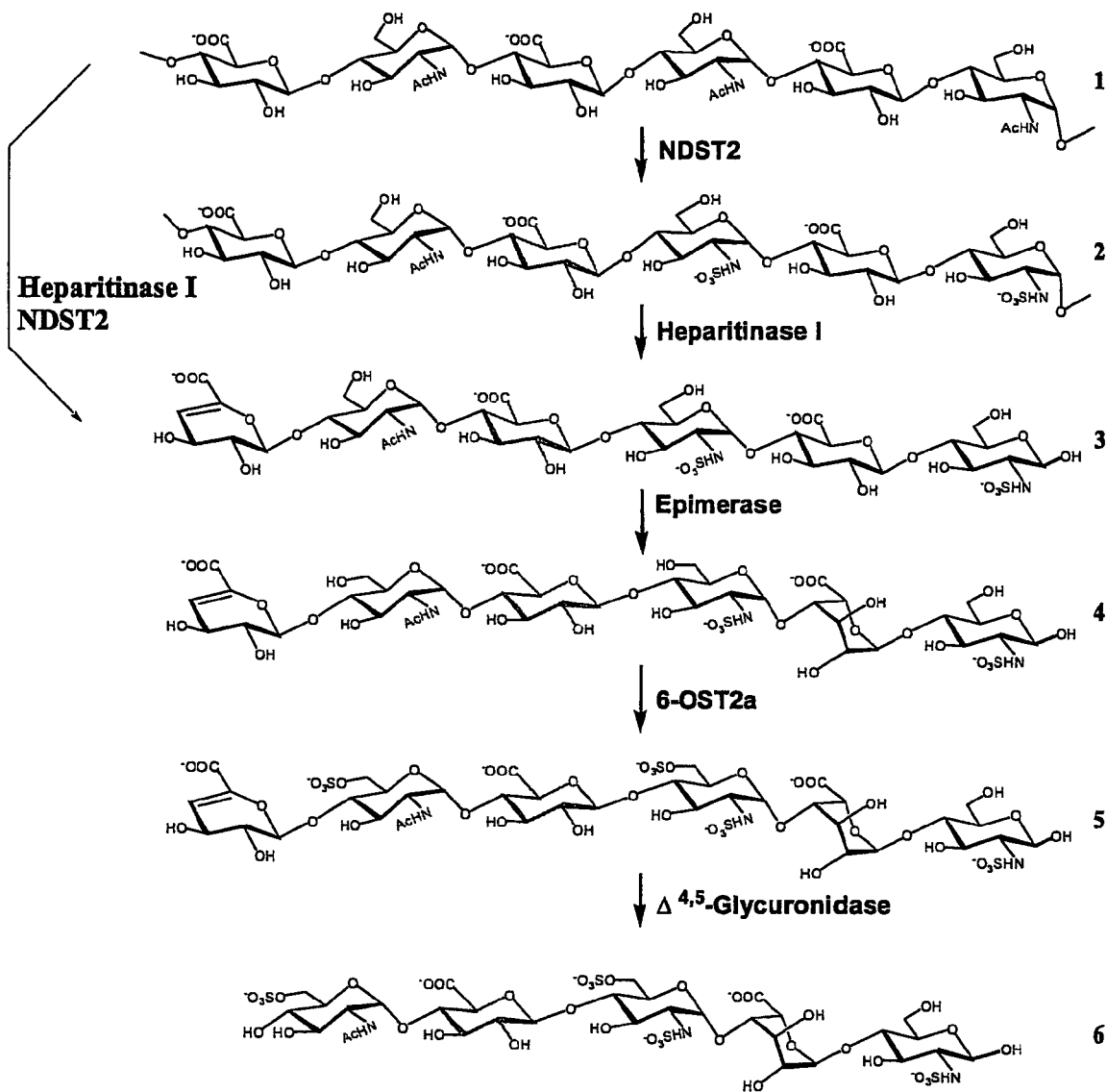
FIG. 6 depicts a reaction scheme for the synthesis of an epimerically enriched, depolymerized heparosan pentasaccharide, as in FIG. 5, with the addition of 6OST2a in the reaction mix, in order to generate O-sulfated pentasaccharides.
Figure 7:
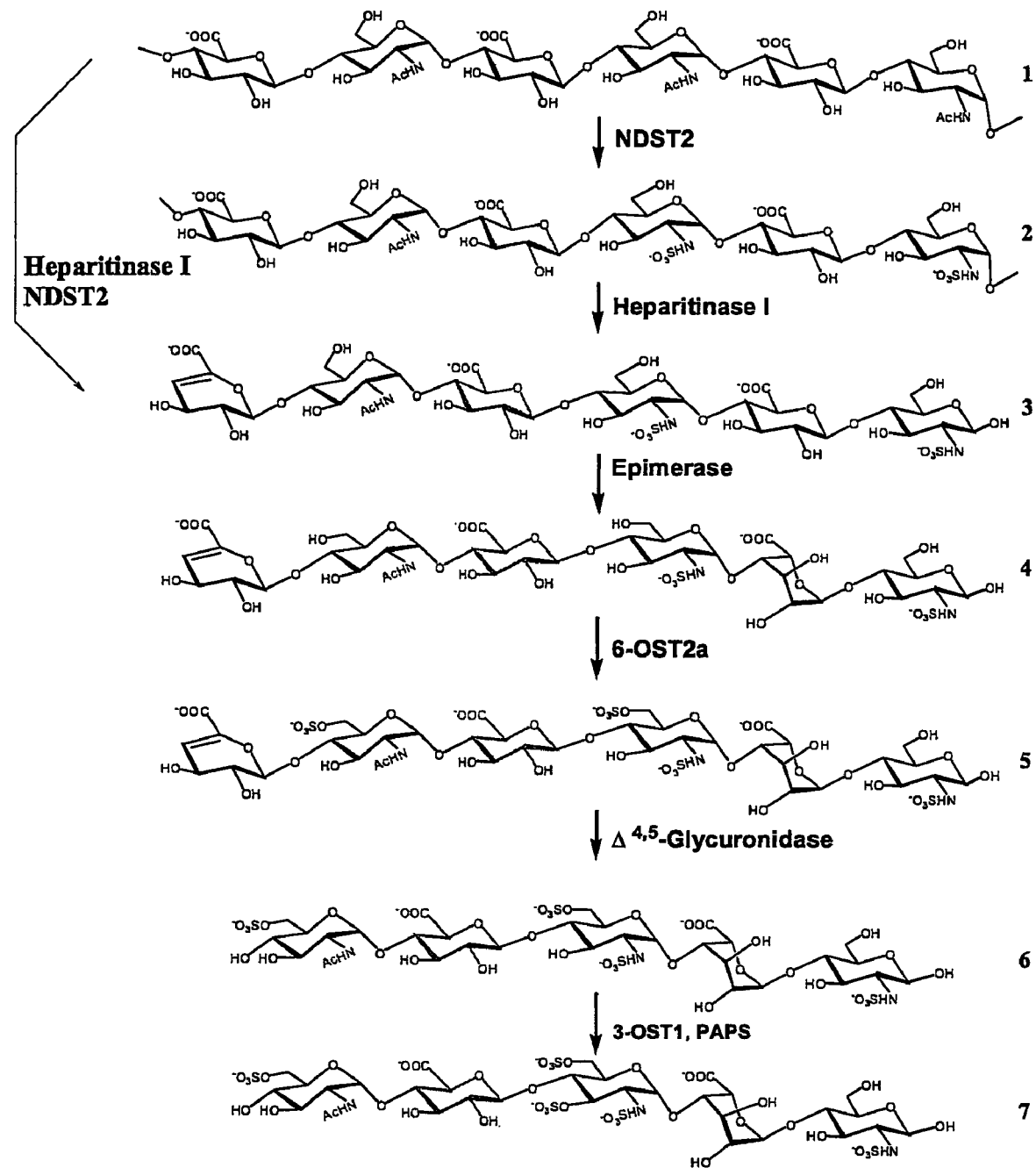
FIG. 7 depicts a reaction scheme for the synthesis of an epimerically enriched, depolymerized heparosan pentasaccharide, as in FIG. 6, with the addition of 3OST1, for further sulfation of the heparosan pentasaccharide.

The inclusion of 6OST2a in the reaction mix may be accomplished as well, as depicted in FIG. 6, to generate O-sulfated pentasaccharides. Similarly, 3OST1 may be incorporated in the reaction mix as well, as depicted in FIG. 7, for further sulfation of the heparosan pentasaccharide.

What is claimed is:

1. A process for the synthesis of an epimerically enriched form of a sulfated heparosan polysaccharide, comprising contacting an acceptor heparosan polysaccharide with the following in a mixture:
   (i) a 3'-phosphoadenosine 5'-phosphosulfate (PAPS) sulfate donor;
   (ii) at least one sulfotransferase;
   (iii) a p-nitrophenyl sulfate sulfate donor;
   (iv) an aryl sulfatase; and
   (v) an epimerase;
wherein:
   (a) said at least one sulfotransferase catalyzes sulfate transfer from said PAPS sulfate donor to said acceptor heparosan polysaccharide;
   (b) said PAPS, by donating said sulfate group is converted to a 3',5'-diphosphoadenosine (PAP);
   (c) said aryl sulfatase catalyzes sulfate transfer from said p-nitrophenyl sulfate sulfate donor to said PAP, thereby regenerating PAPS; and
   (d) said epimerase catalyzes conversion of said acceptor heparosan polysaccharide to its epimer;
thereby synthesizing an epimerically enriched form of a sulfated heparosan polysaccharide in which the uronic acid residues are not sulfated.

2. The process of claim 1, wherein said acceptor heparosan polysaccharide is characterized by the structure of the formula I:

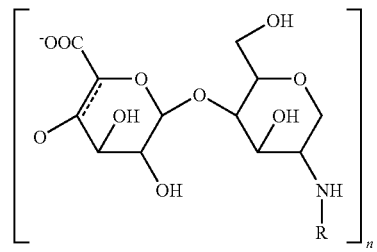

wherein R is a hydrogen, hydroxy, acetyl, alkoxy carbonyl, amido, alkylamido, dialkylamido, nitro, amino, alkylamino, dialkylamino, carboxyl, thio or thioalkyl group, and n is an integer.

3. The process of claim 1, wherein said acceptor heparosan polysaccharide is characterized by the structure of the formula II:

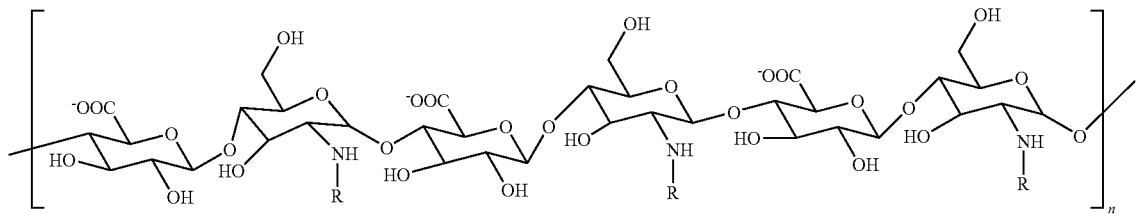

wherein R is a hydrogen, hydroxy, acetyl, alkoxy carbonyl, amido, alkylamido, dialkylamido, nitro, amino, alkylamino, dialkylamino, carboxyl, thio or thioalkyl group, and n is an integer.

4. The process of claim 1, wherein said acceptor heparosan polysaccharide comprises by the structure of the formula III:

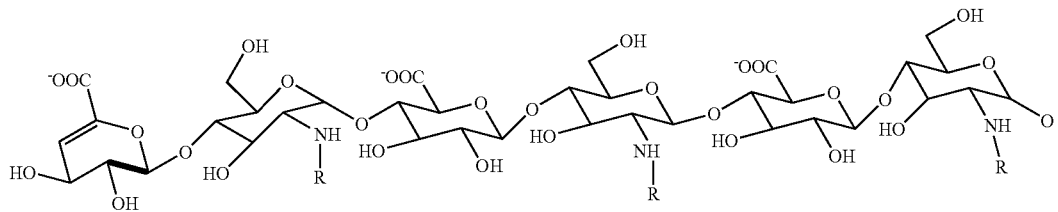

wherein R is a hydrogen, hydroxy, acetyl, alkoxy carbonyl, amido, alkylamido, dialkylamido, nitro, amino, alkylamino, dialkylamino, carboxyl, thio or thioalkyl group, and n is an integer.

5. The process of claim 1, wherein said acceptor heparosan polysaccharide is characterized by the structure of the formula IV:

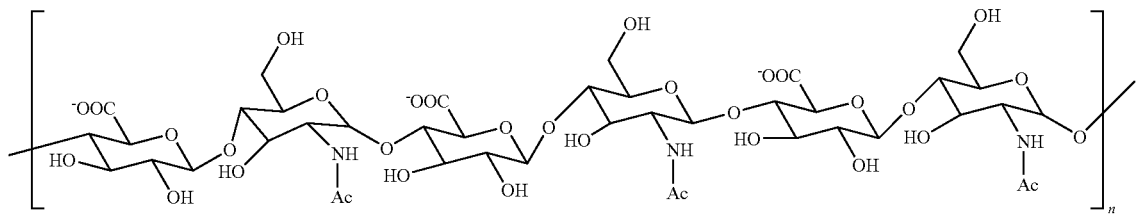

and n is an integer.

6. The process of claim 1, wherein said epimerase is a glucuronosyl C5 epimerase.

7. The process of claim 1, wherein said p-nitrophenyl sulfate donor is at a concentration that is at least one hundred fold in excess of the concentration of PAPS in said mixture.

8. The process of claim 1, wherein said p-nitrophenyl sulfate donor is at a concentration that is at least five hundred fold in excess of the concentration of PAPS in said mixture.

9. The process of claim 1, wherein said reaction mixture further comprises an endoglycosidase, which catalyzes cleavage of a glycosidic linkage in said acceptor heparosan polysaccharide or in said acceptor heparosan polysaccharide epimer.

10. The process of claim 9, wherein said endoglycosidase catalyzes cleavage of a glycosidic linkage in said acceptor heparosan polysaccharide or in said acceptor heparosan polysaccharide epimer, prior to sulfation of said acceptor heparosan polysaccharide or said acceptor heparosan polysaccharide epimer.

11. The process of claim 9, wherein said endoglycosidase catalyzes cleavage of a glycosidic linkage in said acceptor heparosan polysaccharide or in said acceptor heparosan polysaccharide epimer, following sulfation of said acceptor heparosan polysaccharide or said acceptor heparosan polysaccharide epimer.

12. The process of claim 9, wherein said endoglycosidase is a heparitinase or a glycuronidase.

13. The process of claim 12, wherein said endoglycosidase is heparitinase and wherein said heparatinase is heparatinase I, heparitinase II or heparitinase III.

14. The process of claim 12, wherein said endoglycosidase is glycuronidase and wherein said glycuronidase is $\Delta^{4,5}$-glycuronidase.

15. The process of claim 1, wherein said acceptor heparosan polysaccharide is at a final concentration of 0.1-100 mM in said mixture.

16. The process of claim 1, further comprising isolating the epimerically enriched sulfated heparosan polysaccharide from the mixture.

17. The process of claim 1, wherein said sulfotransferase is an N-deacetylase-N-sulfotransferase (NDST), heparin/heparin sulfate N-sulfotransferase; heparin sulfate 2-sulfotransferase; 6-O sulfotransferase (6-OST); 3-O sulfotransferase (3-OST); 2-O sulfotransferase; or a combination thereof.

18. The process of claim 17, wherein said sulfotransferase is NDST and wherein said NDST is selected from the group consisting of NDST1, NDST2, NDST3 or NDST4.

19. The process of claim 17, wherein said sulfotransferase is 3-OST and wherein said 3-OST is 3-OST1.

20. The process of claim 17, wherein said sulfotransferase is 6-OST and wherein said 6-OST is 6-OST1, 6-OST2 or 6-OST3.

21. The process of claim 20, wherein said 6-OST is 6-OST2 and wherein said 6-OST2 is 6-OST2a or 6-OST2b.

* * * * *

UNITED STATES PATENT AND TRADEMARK OFFICE
CERTIFICATE OF CORRECTION

PATENT NO. : 7,655,445 B2  Page 1 of 1
APPLICATION NO. : 10/986058
DATED : February 2, 2010
INVENTOR(S) : Rosenberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 894 days.

Signed and Sealed this

Twenty-eighth Day of December, 2010

David J. Kappos
*Director of the United States Patent and Trademark Office*